US012121360B2

(12) United States Patent
Huggins et al.

(10) Patent No.: US 12,121,360 B2
(45) Date of Patent: Oct. 22, 2024

(54) BRAIN-COMPUTER INTERFACE FOR FACILITATING DIRECT SELECTION OF MULTIPLE-CHOICE ANSWERS AND THE IDENTIFICATION OF STATE CHANGES

(71) Applicant: THE REGENTS OF THE UNIVERSITY OF MICHIGAN, Ann Arbor, MI (US)

(72) Inventors: Jane E. Huggins, Fenton, MI (US); Seth Warschausky, Ann Arbor, MI (US); Ramses Eduardo Alcaide, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 768 days.

(21) Appl. No.: 17/368,207

(22) Filed: Jul. 6, 2021

(65) Prior Publication Data
US 2021/0330242 A1 Oct. 28, 2021

Related U.S. Application Data

(63) Continuation of application No. 15/305,030, filed as application No. PCT/US2015/032192 on May 22, 2015, now Pat. No. 11,266,342.
(Continued)

(51) Int. Cl.
*G06F 3/01* (2006.01)
*A61B 5/00* (2006.01)
(Continued)

(52) U.S. Cl.
CPC ............ *A61B 5/4088* (2013.01); *A61B 5/372* (2021.01); *A61B 5/374* (2021.01); *A61B 5/378* (2021.01);
(Continued)

(58) Field of Classification Search
CPC ....... A61B 5/378; A61B 5/7264; A61B 5/742; G06F 3/015; G09B 7/06
See application file for complete search history.

(56) References Cited

U.S. PATENT DOCUMENTS

| | | | |
|---|---|---|---|
| 5,325,862 | A | 7/1994 | Lewis et al. |
| 5,339,826 | A | 8/1994 | Schmidt et al. |

(Continued)

FOREIGN PATENT DOCUMENTS

| | | | |
|---|---|---|---|
| CN | 102098639 | A | 6/2011 |
| CN | 103092340 | A | 5/2013 |

(Continued)

OTHER PUBLICATIONS

Amyotrophic Lateral Sclerosis (ALS) Fact Sheet, National Institute of Neurological Disorders and Stroke (Jun. 2013).
(Continued)

*Primary Examiner* — Gary Collins
(74) *Attorney, Agent, or Firm* — MARSHALL, GERSTEIN & BORUN LLP

(57) ABSTRACT

Methods, systems, apparatus, and non-transitory computer readable media are disclosed utilizing brain-computer interfaces (BCIs). Various embodiments are disclosed to allow a user to directly select multiple-choice answers, to provide motorized wheelchair controls, and to allow a user to play a game via the BCI. When used in a cognitive assessment test, embodiments include the administration of unmodified standardized tests with results in the same or a similar format as those taken without a BCI. Various embodiments are disclosed to improve the accuracy of BCI test administration using a three-step process for each test question, which includes determining whether the user intends to select an answer, monitoring user brain activity to determine a selected answer, and verifying the selected answer. In addition, the selected answer may be verified by monitoring user
(Continued)

brain activity in accordance with a hold-release process to determine whether a user intends to initiate a state change.

10 Claims, 5 Drawing Sheets

Related U.S. Application Data

(60) Provisional application No. 62/005,243, filed on May 30, 2014.

(51) Int. Cl.

| | |
|---|---|
| A61B 5/372 | (2021.01) |
| A61B 5/374 | (2021.01) |
| A61B 5/378 | (2021.01) |
| A61F 2/72 | (2006.01) |
| A61F 4/00 | (2006.01) |
| G09B 7/06 | (2006.01) |

(52) U.S. Cl.
CPC .......... *A61B 5/7221* (2013.01); *A61B 5/7264* (2013.01); *A61B 5/7267* (2013.01); *A61B 5/7282* (2013.01); *A61B 5/742* (2013.01); *A61B 5/7435* (2013.01); *A61F 2/72* (2013.01); *A61F 4/00* (2013.01); *G06F 3/015* (2013.01); *G09B 7/06* (2013.01)

(56) References Cited

U.S. PATENT DOCUMENTS

| | | | |
|---|---|---|---|
| 5,692,517 | A | 12/1997 | Junker |
| 5,967,996 | A | 10/1999 | Kadota et al. |
| 7,120,486 | B2 | 10/2006 | Leuthardt et al. |
| 8,155,736 | B2 | 4/2012 | Sullivan et al. |
| 8,244,475 | B2 | 8/2012 | Aguilar et al. |
| 9,743,002 | B2 | 8/2017 | Wierich |
| 2002/0036381 | A1 | 3/2002 | Scibetta |
| 2002/0065851 | A1 | 5/2002 | Watson et al. |
| 2003/0031457 | A1 | 2/2003 | Miomo et al. |
| 2003/0195798 | A1 | 10/2003 | Goci |
| 2003/0203342 | A1 | 10/2003 | Bowers |
| 2004/0043372 | A1 | 3/2004 | Jebb et al. |
| 2004/0092809 | A1 | 5/2004 | DeCharms |
| 2004/0169673 | A1 | 9/2004 | Crampe et al. |
| 2004/0249302 | A1 | 12/2004 | Donoghue et al. |
| 2005/0017870 | A1 | 1/2005 | Allison et al. |
| 2005/0085744 | A1 | 4/2005 | Beverina et al. |
| 2005/0131311 | A1 | 6/2005 | Leuthardt et al. |
| 2005/0170325 | A1 | 8/2005 | Steinberg et al. |
| 2005/0191609 | A1 | 9/2005 | Fadel et al. |
| 2005/0222873 | A1 | 10/2005 | Nephin et al. |
| 2007/0066914 | A1 | 3/2007 | Le et al. |
| 2007/0086773 | A1 | 4/2007 | Ramsten et al. |
| 2007/0166675 | A1 | 7/2007 | Atkins et al. |
| 2007/0166686 | A1 | 7/2007 | Foster |
| 2008/0218472 | A1 | 9/2008 | Breen et al. |
| 2008/0317206 | A1 | 12/2008 | Yoshino |
| 2009/0099623 | A1 | 4/2009 | Bentwich |
| 2010/0010391 | A1 | 1/2010 | Skelton et al. |
| 2010/0039438 | A1 | 2/2010 | Kennedy |
| 2010/0069780 | A1* | 3/2010 | Schuette .................. G06F 3/015 600/547 |
| 2010/0100001 | A1 | 4/2010 | Aguilar et al. |
| 2010/0240016 | A1 | 9/2010 | Ween et al. |
| 2010/0317988 | A1 | 12/2010 | Terada et al. |
| 2011/0148927 | A1 | 6/2011 | Tainsh et al. |
| 2011/0152710 | A1 | 6/2011 | Kim et al. |
| 2011/0301486 | A1 | 12/2011 | Van Hek et al. |
| 2012/0034583 | A1 | 2/2012 | Dujowich et al. |
| 2012/0044154 | A1 | 2/2012 | Black et al. |
| 2012/0150545 | A1 | 6/2012 | Simon |
| 2012/0254745 | A1 | 10/2012 | SanGiovanni et al. |
| 2012/0289854 | A1 | 11/2012 | Yamada et al. |
| 2013/0130799 | A1 | 5/2013 | Van Hulle et al. |
| 2014/0058528 | A1 | 2/2014 | Contreras-Vidal et al. |
| 2014/0065594 | A1 | 3/2014 | Venable |
| 2016/0253890 | A1 | 9/2016 | Rabinowitz et al. |

FOREIGN PATENT DOCUMENTS

| | | | |
|---|---|---|---|
| EP | 2613222 | A1 | 7/2013 |
| JP | 11-065794 | | 3/1999 |
| JP | 2002-236957 | A | 8/2002 |
| JP | 2003-058298 | A | 2/2003 |
| JP | 2010-015584 | A | 1/2010 |
| JP | 2012-053656 | A | 3/2012 |
| JP | 2013-004006 | A | 1/2013 |
| WO | WO-02/091119 | A2 | 11/2002 |
| WO | WO-03/037231 | A1 | 5/2003 |
| WO | WO-2004/073485 | A2 | 9/2004 |
| WO | WO-2005/079332 | A2 | 9/2005 |
| WO | WO-2006/051709 | A1 | 5/2006 |
| WO | WO-2007/044431 | A2 | 4/2007 |
| WO | WO-2009/056650 | A1 | 5/2009 |
| WO | WO-2011/10500 | A1 | 1/2011 |
| WO | WO-2011/105000 | A1 | 9/2011 |
| WO | WO-2011/140303 | A1 | 11/2011 |
| WO | WO-2012/020906 | A1 | 2/2012 |
| WO | WO-2012/071544 | A2 | 5/2012 |
| WO | WO-2013/012739 | A1 | 1/2013 |

OTHER PUBLICATIONS

Aref et al., The P300-Certainty Algorithm: Improving accuracy by withholding erroneous selections, ECNS Conference, Bristol, TN, Sep. 12-16, 2012, p. 79.

Bai et al., Exploration of computational methods for classification of movement intention during human voluntary movement from single trial EEG, *Clin. Neurophysiol.*, 118:2637-2655 (2007).

Bai et al., Towards a user-friendly brain-computer interface: Initial tests in ALS and PLS patients, *Clin. Neurophysiol.*, 121:1293-303 (2010).

Bashashati et al., "A Survey of signal processing algorithms in brain-computer interfaces based on electrical brain signals," *J. Neural Eng.*, 4:R32-R57 (2007).

Cipresso et al., "The combined use of Brain Computer Interface and Eye-Tracking technology for cognitive assessment in Amyotrophic Lateral Sclerosis," 2011 5th International Conference on Pervasive Computing Technologies for Healthcare (PervasiveHealth) and Workshops (May 23, 2011).

Cipresso et al., "The use of P300-based BCIs in amyotrophic lateral sclerosis: from augmentative and alternative communication to cognitive assessment," Brain and Behavior 2(4):479-498 (Mar. 13, 2012).

Connolly et al., "Innovations in neuropsychological assessment using event-related brain potentials," *International Journal of Psycholophysology* 37 (Jul. 2000), pp. 31-47.

Connolly et al., "Performance on WISC-111 and WAIS-R NI Vocabulary Subtests Assessed with Event-Related Brain Potentials: An Innovative Method of Assessment," *Journal of Clinical and Experimental Neuropsychology*, vol. 21, (Aug. 9, 2010), pp. 444-464.

D'Arcy et al., "Electrophysiological assessment of language function following stroke," *Clin. Neurophysiol.*, 114:662-72 (2003).

D'Arcy, "Evaluation of reading comprehension with neuropsychological and event-related brain potential (ERP) methods," *Journal of the International Neuropsychological Society* (Jul. 2000), pp. 556-567.

European Patent Application No. 15799099, Supplementary Partial European Search Report, dated Jan. 3, 2018.

European Patent Application No. 15799099.5, Extended European Search Report, dated Apr. 19, 2018.

Hampshire et al., "Assessing residual reasoning ability to overtly non-communicative patients using fMRI," *NeuroImage: Clinical* (Nov. 30, 2012).

International Preliminary Report on Patentability, International Application No. PCT/US2015/032192, dated Dec. 6, 2016.

(56) References Cited

OTHER PUBLICATIONS

International Search Report and Written Opinion, International application No. PCT/US2015/032192, mailed Aug. 31, 2015.
Iverson et al., "A brain-computer interface tool to assess cognitive funcitons in completely paralyzed patients with amyotrophic lateral sclerosis," *Clinical Neurophysiology* 119 (Aug. 31, 2008) pp. 2214-2223.
Kubler et al., "Brain-computer interfaces and communication in paralysis: Extinction of goal directed thinking in completely paralysed patients?" *Clinical Neurophysiology*, 119, (2008) 2658-2666.
Makeig et al., "Evolving signal processing for brain-computer interfaces" Proc. of the IEEE, 100:1567-84 (2012).
Martens et al., Overlap and refractory effects in a brain-computer interface speller based on the visual P300 event-related potential, J. Neural Eng., 6:026003 (2009).
Naci et al., Brain-computer interfaces for communication with nonresponsive patients, *Ann. Neurol.*, 72:312-323 (2012).
Perego et al., "Cognitive ability assessment by Brain-Computer Interface Validation of a new assessment method for cognitive abilities," *Journal of Neuroscience Methods* 201:239-250 (2011).
Power et al., Towards a system-paced near-infrared spectroscopy brain computer interface: differentiating prefrontal activity due to mental arithmetic and mental singing from the no-control states; J. Neural Eng., 8(6):66004 (2011).
Ramos-Murguialday et al., Brain-computer interface for a prosthetic hand using local machine control and haptic feedback, pp. 609-613, Proceedings of the 2007 IEEE 10th International Conference on Rehabilitation Robotics, Jun. 12-15, Noordwijk, the Netherlands (2007).
Sellers et al., "A P300-based brain-computer interface: Initial tests by ALS patients," *Clinical Neurophysiology* 117, (2006) 538-548.
Seo et al., Discrimination of "yes" and "no" responses by auditory stimuli multiple-choice questions in human EEG, IEEE Computer Society, IEEE International Conference on Convergence Information Technology, pp. 1127-1133 (2007).
Sorger et al., Another kind of BOLD Response: answering multiple-choice questions via online decoded single-trial brain signals, In: Laureys et al. (eds.), Progress in Brain Research, vol. 177, Chapter 19, pp. 275-292 (2009).
Thompson et al., "Performance assessment in brain-computer interface-based augmentative and alternative communication," *BioMedical Engineering OnLine*, (2013) 12:43.
Thompson et al., Classifier-based latency estimation: a novel way to estimate and predict BCI accuracy, *J. Neural Eng.* 10:016006 (2013).
Vieru, Brain Computer Interface Can Stimulate the Cortext, Softpedia (Feb. 16, 2010).
Zander et al., "Towards passive brain-computer interfaces: applying brain-computer interface technology to human-machine systems in general," *J. Neural Eng.* 8 (Mar. 24, 2011).
Examination Report from European Application No. 15799099.5 dated Oct. 18, 2021.

\* cited by examiner

BRAIN-COMPUTER INTERFACE FOR FACILITATING DIRECT SELECTION OF MULTIPLE-CHOICE ANSWERS AND THE IDENTIFICATION OF STATE CHANGES

CROSS-REFERENCE TO RELATED APPLICATION

This application is a Continuation of U.S. application Ser. No. 15/305,030 filed Apr. 18, 2017, which is a U.S. national phase of PCT/US1/23192, filed May 22, 2015, which claims the priority benefit under 35 U.S.C. § 119(e) of U.S. Provisional Patent Application No. 62/005,243, filed May 30, 2014, the disclosures of which are incorporated herein by reference in their entirety.

STATEMENT OF GOVERNMENTAL INTEREST

This invention was made with government support under TR000433, HD054913, and HD054697, awarded by the National Institutes of Health, and under H133G090005, awarded by the Department of Education. The Government has certain rights in the invention.

FIELD OF THE DISCLOSURE

The present disclosure relates to systems, methods, and apparatus for a brain-computer interface (BCI) and, more particularly, to a BCI implementing a multi-step process to facilitate direct standardized cognitive testing and the identification of a user's desired selections and changes to one or more selections, actions, and/or states.

BACKGROUND

For many patients with neurological conditions, cognitive assessments may impact their quality of life by allowing medical personnel to determine interventions and/or services that they may need to receive. But patients with neurological conditions may not be able to participate in such assessments due to motor and/or speech impairments. Furthermore, attempts to implement BCIs to administer cognitive assessment testing to patients with motor and/or speech impairments present several issues.

First, BCIs typically used for cognitive testing often implement indirect methods. For example, the BCI may allow a patient to move a cursor on a screen to select a test question. Indirect methods do not provide a patient with the precision and control necessary to quickly select an answer, and a patient may become distracted or frustrated during the test, which may skew the test results. Second, and potentially compounding these inaccuracies, indirect BCI cognitive assessment testing procedures typically require that the cognitive test be modified from the original standardized version to include the adaptive elements of indirect question selection. Therefore, providing a cognitive assessment test that provides accurate results in accordance with a standardized cognitive test format presents several challenges.

DETAILED DESCRIPTION

Figure 1:
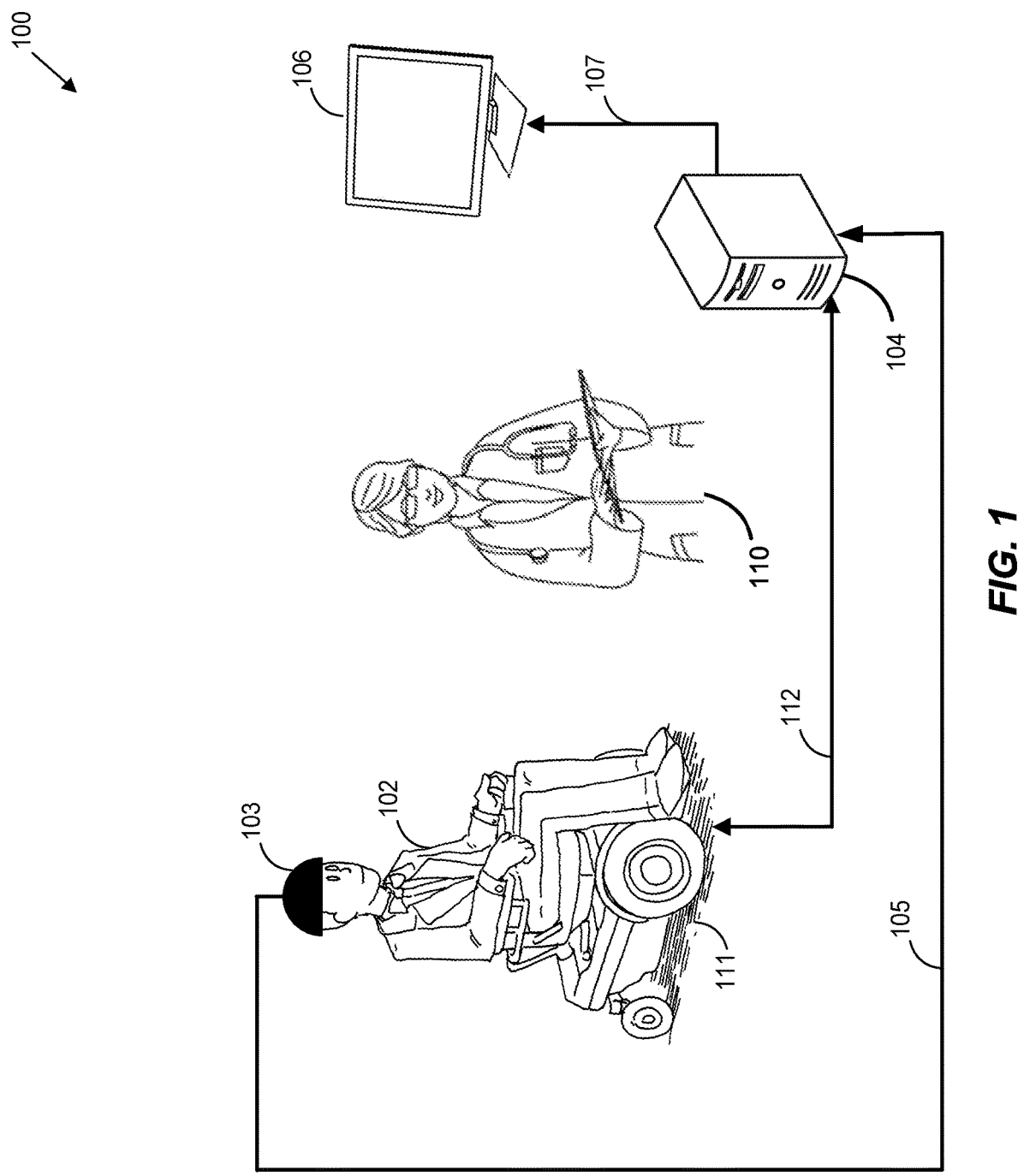
FIG. 1 is a block diagram of a brain-computer interface (BCI) testing system 100 in accordance with an exemplary embodiment of the present disclosure.

FIG. 1 is a block diagram of a brain-computer interface (BCI) system 100 in accordance with an exemplary embodiment of the present disclosure. BCI system 100 may include a user 102, a brain activity monitoring system 103, a BCI 104, a display 106, and a test administrator 110.

As shown in FIG. 1, a user 102 may participate in a cognitive assessment test that is overseen by test administrator 110. The test administrator may assist in the test-taking procedure by, for example, accessing a test file from BCI 104, recording observations while the test is being administered to user 102, saving the answers to the test once it has been completed, etc.

In some embodiments, BCI system 100 may be implemented as part of a cognitive test assessment procedure. For example, BCI system 100 may facilitate the administration of one or more cognitive tests based on user 102's brain activity and without utilizing motor and/or oral feedback from user 102. Such an embodiment could be particularly useful when user 102 is "locked-in" due to a specific impairment, and cannot readily communicate otherwise in any viable physical manner.

The user's brain activity may include activity that is collected in response to a user being exposed to one or more stimuli, such as visual stimuli displayed on display 106 and/or other types of stimuli, such as auditory tones, etc. Stimuli other than those displayed via display 106 are not shown in FIG. 1 for purposes of brevity. In an embodiment, test questions may be displayed via display 106, as shown in FIG. 1, and each multiple-choice question may have an associated visual stimuli associated therewith, which is further discussed below. Based upon an analysis of user 102's brain activity while looking at (or otherwise paying attention to, being exposed to, focusing on, concentrating on, etc.) a particular multiple choice answer, BCI 104 may determine user 102's selection by correlating user 102's brain activity to the particular unique visual stimuli associated with that answer.

In various embodiments, brain activity monitoring system 103 may be implemented as one or more electroencephalograph (EEG) measurement devices and may include any suitable number of electrodes and/or sensors. In accordance with such embodiments, the electrodes and/or sensors may be attached to any suitable portion of the user's head, etc. Various embodiments of brain activity monitoring system 103 may include any combination of invasive and/or non-invasive electrode sensors. Brain activity monitoring system 103 may be configured to measure a user's brain activity via any suitable number of electrodes and/or sensors in accordance with any suitable number and/or type of standards, protocols, etc. Brain activity monitoring system 103 may be configured to convert and/or transmit the user's brain activity to BCI 104 as one or more data signals in accordance with any suitable number and/or type of communication formats, protocols, and/or standards, such as via link 105, for example.

To provide another example, in accordance with an embodiment, brain activity monitoring system 103 may be configured to measure a user's brain activity as one or more events within EEG bands such as Delta bands, Theta bands, Alpha bands, Beta bands, Gamma bands, and/or Mu bands. In an embodiment, brain activity monitoring system 103 may be configured to monitor one or more event-related potential (ERP) components elicited by the user in the response to one or more choices presented to the user via display 106.

BCI 104 may be implemented as any suitable device configured to receive data signals from brain activity monitoring system 103, to analyze and/or process these signals, and/or to transmit one or more data signals to display 106 to provide feedback to user 102. For example, BCI 104 may be implemented as a user equipment (UE), such as a mobile device, a computer, laptop, tablet, desktop, one or more parts of a gaming system, one or more parts of a powered wheelchair controller system, one or more parts of any suitable device that is configured to render assistance to a user lacking motor and/or oral skills, or any other suitable type of computing device.

Although shown in FIG. 1 as a single link 105, communications between BCI 104 and brain activity monitoring system 103 may be implemented with any appropriate combination of wired and/or wireless communication networks, wires, buses, wireless links, etc., to facilitate these communications. For example, BCI 104 and/or brain activity monitoring system 103 may utilize any combination of wired and/or wireless links, local area networks (LANs), etc.

As a result of processing and/or analyzing of the received data signals from brain activity monitoring system 103, various embodiments include BCI 104 facilitating the administration of a cognitive assessment test by performing one or more functions such as, for example, determining user 102's intent to provide an answer to multiple-choice questions displayed on display 106, determining user 102's answer selections, and/or verifying user 102's answer selections, which are further discussed below.

BCI 104 may be configured to transmit one or more data signals to display 106 and/or to another external generator of stimuli (not shown in FIG. 1) based upon these functions, such that display 106 may display stimuli to the user corresponding to the multiple-choice questions, the user's answer selections, and/or images to user 102 while user 102 is taking the test.

BCI 104 may be configured to transmit one or more data signals to display 106 to cause display 106 to display one or more images, to modify the images, and/or to display additional images in response to the measurements of the user's brain activity received from brain activity monitoring system 103. For example, BCI 104 may determine user 102's answer selection, for example, from data signals representative of the user's brain activity that are received from brain activity monitoring system 103 while the user is exposed to a displayed stimuli corresponding to user 102's answer selection.

Display 106 may be configured to display information in response to the one or more data signals received from BCI 104, which may be received via any suitable number and/or type of communication links (e.g., link 107). Although display 106 is illustrated in FIG. 1 as being separate from BCI 104, various embodiments include display 106 being integrated as part of BCI 104, display 106 being co-located within, or proximate to, BCI 104, etc. As will be appreciated by those of ordinary skill in the relevant art(s), the integration, coupling, and/or interactive functionality between BCI 104 and display 106 may depend on which of these implementations is utilized for a particular application.

Again, BCI 104 may be configured to cause display 106 to display one or more test questions and/or audio prompts to determine a user's response to these questions by analyzing and/or processing signals received from brain activity monitoring system 103. In various embodiments, BCI 104 may be configured to facilitate the cognitive assessment of a user in accordance with any suitable cognitive test format, which may include standardized or non-standardized tests. In accordance with embodiments in which BCI 104 facilitates the administration of standardized cognitive tests, BCI 104 may be configured to format the user's answers in accordance with the respective standardized test format. In this way, BCI 104 allows standard grading methods to be used for standardized tests taken with BCI system 100.

In various cognitive test assessment embodiments, BCI 104 may be configured to process data signals received via brain activity monitoring system 103 as part of a three-step process to determine user 102's answer to the multiple-choice questions displayed on display 106. With regards to the analysis of the user's brain activity, various embodiments may include BCI 104 executing one or more algorithms, instructions, programs, applications, code, etc., to facilitate these functions. For example, BCI 104 may interpret signals received from brain activity monitoring system 102 using classification systems such as neural networks, stepwise linear discriminate analysis, support vector machines, etc., to determine a probability that the user has selected one of the displayed answers.

As the first step in this process, a determination may be made based upon an analysis of data signals received via brain activity monitoring system 103 that user 102 intends to answer the multiple-choice questions. That is, BCI 104 may be configured to analyze user 102's brain activity as part of this first step to ensure that user 102 is focusing on taking the test, and is not distracted by external stimuli and/or not paying attention to the displayed images.

In other words, during the first step, BCI 104 may determine that user 102 intends to decide upon an answer to the multiple-choice questions displayed on display 106. In various embodiments, this first step may be implemented using any suitable method to determine user 102's intention. For example, BCI 104 may implement one or more asynchronous BCI processing methods to make this determination.

To provide another example, during the first step, BCI 104 may wait for a predetermined period of time before accepting an answer from user 102. This time period, which may be indicated by a timer shown on display 106 that does not block or otherwise interfere with the displayed images, may indicate an allotted time to allow user 102 to decide on an answer before the timer expires. In accordance with embodiments utilizing a timer for the determination of whether the user intends to decide upon an answer. BCI 104 may make this determination when the timer has started.

In a second step, BCI 104 may determine user 102's answer from among the test answers associated with the multiple-choice questions displayed on display 106 once it has been decided that user 102 intends to provide an answer. In various embodiments, BCI 104 may be configured to implement any suitable BCI process or combination of suitable BCI processes to determine user 102's answer. For example, BCI 104 may generate images via display 106 in accordance with a steady state visual invoked potential process and analyze user 102's brain activity in accordance with this process to determine user 102's selection.

To provide other examples, BCI 104 may analyze user 102's brain activity in accordance with P300 responses using any of a number of arrangements for displaying the image stimuli via display 106, such as a grid format, rapid serial visual presentation, etc.

In a third step, BCI 104 may verify the user's answer from the second step. In various embodiments, BCI 104 may continue to receive and analyze the user's brain activity by executing one or more algorithms, instructions, programs, applications, code, etc., after the user's selected answer has been determined by BCI 104 to verify the user's answer. For example, various embodiments include BCI 104 implementing error potential detection, which may result in BCI 104 causing display 106 to display an answer that was interpreted as chosen by the user, and then determining whether the user's brain activity produced an error potential.

To provide another example, BCI 104 may cause display 106 to display one or more images that allow user 102 to confirm or cancel the selected answer that been determined by BCI 104 in the second step, which is displayed to user 102 via display 106. To provide another example, BCI 104 may cause display 106 to repeat the second step and compare the results of both selections to verify a match.

To provide yet another example, BCI 104 may be configured to execute a hold-release algorithm with respect to two different states. The first of these states may represent user 102 holding the initial answer selection, which is displayed to user 102 via display 106 after the second step. The second of these states may represent user 102 changing his selection to another stimuli displayed via display 102 to cancel the displayed selection after the second step.

That is, embodiments include BCI 104 being configured to cause display 106 to display the selected answer from step 2 and an image indicative of the user's intent to cancel this answer selection. BCI 104 may be configured to execute a hold-release algorithm that associates the retention of the user's focus on the stimuli associated with the displayed answer as a hold state, and the transition of the user focusing on the stimuli associated with the cancellation image as a release state. The details of the hold-release process are further discussed below with reference to FIG. 5.

In this way, BCI system 100 may facilitate the administration of standardized and non-standardized testing via the monitoring of the user's brain activity without the need for motor and/or oral feedback from the user. In addition, BCI system 100 addresses many of the issues regarding accuracy and standardization that typically plague indirect BCI testing procedures. Traditional BCI testing methods typically rely on an analysis of a user's brain activity to select a test answer using indirect methods, such as by moving a cursor around a screen. Indirect testing methods also have issues associated with accuracy and skewing test results, including those related to a user becoming frustrated during the test, which may compound errors and result in an incorrect assessment of the user's cognitive abilities.

In contrast to these indirect approaches, embodiments of BCI system 100 allow user 102 to select answers in a direct way. This provides more accurate results compared to indirect methods, and also provides the added benefit of not requiring a standardized test to be reformatted, which is generally required for indirect testing methods. In other words, direct selection by user 102 better conforms to the protocol for which the standardized test was designed, i.e., a direct selection of multiple-choice answers. By presenting the test in a similar way in which it was designed to be given to everyone (and not just users lacking motor and/or oral skills) BCI system 100 helps to remove test data skewing that is otherwise introduced simply through the manner in which a BCI test is administered.

In other embodiments, BCI system 100 may be implemented as part of a control system configured to render assistance to a user lacking effective motor and/or oral skills For example, BCI 104 may be configured to additionally or alternatively use signals received via brain activity monitoring system 103 and provide control commands to motorized wheelchair 111. In accordance with such embodiments, BCI 104 may be configured to transmit control commands to motorized wheelchair 111 as one or more data signals in accordance with any suitable number and/or type of communication formats, protocols, and/or standards, such as via link 112, for example. Display 106 and/or BCI 104 may be integrated as part of, mounted on, or otherwise associated with motorized wheelchair 111 to facilitate these functions.

In still other embodiments, BCI system 100 may be implemented as part of a gaming system playable by a user lacking effective motor and/or oral skills For example, BCI 104 may be configured to additionally or alternatively use signals received via brain activity monitoring system 103 and modify feedback displayed user 102 via display 106 as part of a gaming application. In accordance with such embodiments, BCI 104 may be configured to transmit one or more data signals to display 106 in accordance with any suitable number and/or type of communication formats, protocols, and/or standards, such as via link 107, for example.

For example, BCI 104 may be configured to implement a hold-release algorithm for this purpose, with the hold state and the release state being associated with any suitable type and/or number of physical actions, commands, etc., such as those used to control motorized wheelchair 111, those used for a gaming application, etc. Similar to the determination of user 102's answers to test questions as previously discussed, BCI 104 may analyze user 102's brain activity as the user focuses on different stimuli displayed on display 106 corresponding to various controls. Based upon user 102's selected function, BCI 104 may determine whether user 102 would like to hold a selected command or transition to a release state representing another command. These embodiments could be particularly useful in situations in which a user wants to use two different types of states to cause a change in a control process that may be represented in such a manner.

To provide an illustrative example, various embodiments include display 106 displaying a particular stimulus for user 102 to focus on (e.g., by counting flashes of an icon). When BCI 104 determines that user 102 is doing so, BCI 104 may interpret the user's focus on the particular stimulus as a holding state, such as the activation of a motorized wheelchair control, for example. The motorized control could be associated with an action such as driving motorized wheelchair 111 forward, backward, turning motorized wheelchair 111, etc. Continuing this example, when BCI 104 detects user 102's initial selection that was made through attention to the stimulus, BCI 104 may cause a command to be issued to motorized wheelchair 111 to drive forward and then maintain that action as the holding state as long as user 102 continues to focus on the stimuli associated with that command.

Further continuing this example, when BCI 104 detects that user 102 has switched his focus to another stimulus (e.g., counting flashes of another icon), BCI 104 may interpret this as a de-activation or a cancellation of a motorized wheelchair control, which represents a release state. That is, the release state may be associated with the cessation of the action associated with the holding state. For example, if the holding state is associated with moving motorized wheelchair 111 forward, then detection of the release state could cause BCI 104 to issue a command to stop motorized wheelchair 111.

In various embodiments in which BCI 104 executes hold-release state algorithms, the algorithms may be applied to any suitable type and/or number of control states. Additional embodiments could include controlling volume by associating a volume increase (or decrease) with a holding state and the cessation of the holding state with the release state. In this way, BCI 104 may provide a user with the ability to exercise any type of control that takes advantage of state changes via analysis of a user's brain activity.

Figure 2:
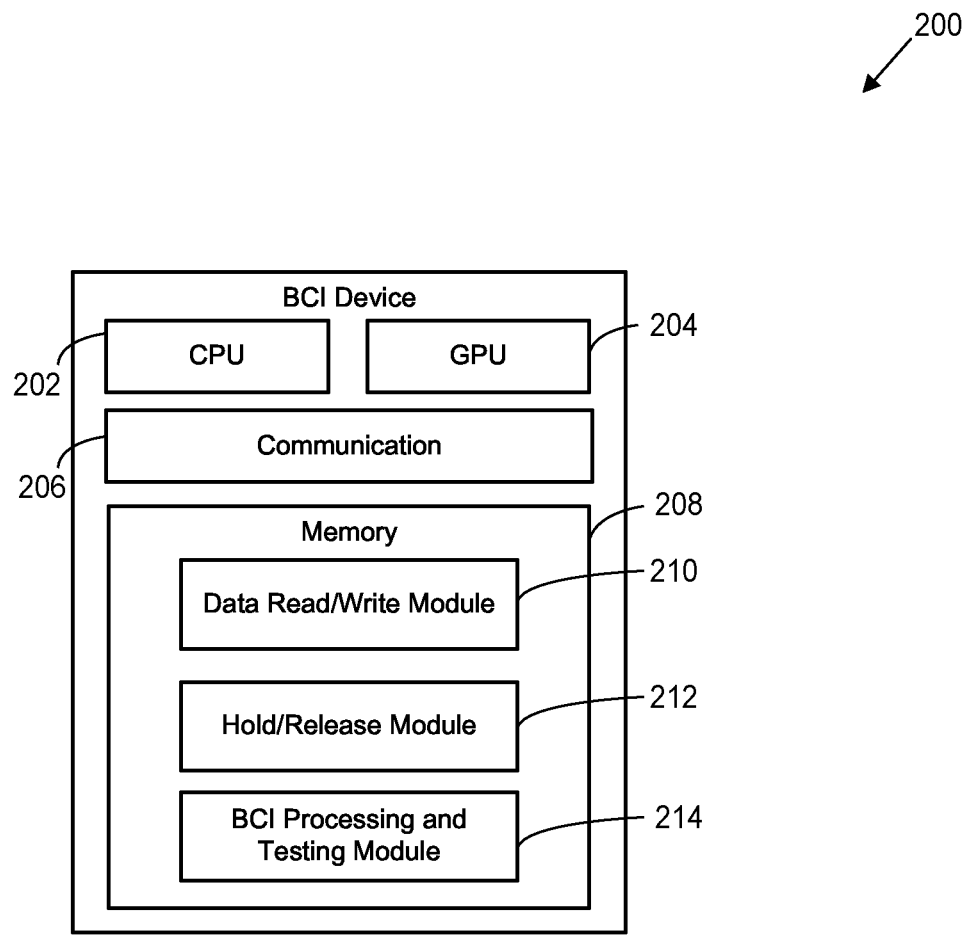
FIG. 2 illustrates a BCI device 200 in accordance with an exemplary embodiment of the present disclosure.

FIG. 2 illustrates a BCI device 200 in accordance with an exemplary embodiment of the present disclosure. BCI device 200 includes a central processing unit 202, a graphics processing unit (GPU) 204, a communication unit 206, and a memory 208. BCI device 200 may be implemented as any computing device suitable for receiving, monitoring, analyzing, and/or processing data signals representative of a user's brain activity. In an embodiment, BCI device 200 is an implementation of BCI 104, as shown in FIG. 1.

In an embodiment, communication unit 206 may be configured to enable the receipt of data from a brain activity monitoring system, such as from brain activity monitoring system 103, for example, as shown in FIG. 1. In various embodiments, communication unit 206 may be configured to facilitate the transfer of data received from a brain activity monitoring system to CPU 202 and/or to memory 208. For example, data received from communication unit 206 from a brain activity monitoring system may be stored in any suitable location in memory 208 for subsequent processing by CPU 202.

Alternatively or additionally, various embodiments of communication unit 206 include communication unit 206 sending one or more commands, signals, data, etc., to one or more control components to facilitate a state change. Examples of control components could include motor controllers, volume controllers, or any suitable type of controller component that may be utilized to assist a user with impaired motor and/or oral skills These control components are not shown in FIG. 2 for purposes of brevity.

As will be appreciated by those of skill in the relevant art(s), communication unit 206 may be implemented with any combination of suitable hardware and/or software to enable these functions. For example, communication unit 206 may be implemented with any number of wired and/or wireless transceivers, network interfaces, physical layers (PHY), etc.

In various embodiments, CPU 202 and/or GPU 204 may be configured to communicate with memory 208 to store to and read data from memory 208. For example, CPU 202 and/or GPU 204 may be implemented as any suitable number and/or type of processors. In various embodiments, CPU 202 may be configured to process brain activity data signals received from a brain activity monitoring system, while GPU 204 may be configured to send data signals and/or commands to a display device, such as display 106, for example, as shown in FIG. 1, to cause the display to show one or more images. In an embodiment, the images that GPU 204 causes to be displayed are used to administer a cognitive assessment test, such as those previously discussed with reference to FIG. 1.

In accordance with various embodiments, memory 208 is a computer-readable non-transitory storage device that may include any combination of volatile (e.g., a random access memory (RAM), or a non-volatile memory (e.g., battery-backed RAM, FLASH, etc.). In various embodiments, memory 208 may be configured to store instructions executable on CPU 208 and/or GPU 204. These instructions may include machine readable instructions that, when executed by CPU 202 and/or GPU 204, cause CPU 202 and/or GPU 204 to perform various acts.

In various embodiments, data read/write module 210, hold-release module 212, and BCI processing and testing module 214 are portions of memory 208 configured to store instructions executable by CPU 202 and/or GPU 204. In various embodiments, data read/write module 210 may include instructions that, when executed by CPU 202 and/or GPU 204, causes CPU 202 and/or GPU 204 to read data from and/or to write data to memory 208. In various embodiments, data read/write module 210 may include instructions that, when executed by CPU 202 and/or GPU 204, causes CPU 202 and/or GPU 204 to receive data from a brain activity monitoring system via communication unit 206. In an embodiment, data read/write module 210 may enable CPU 202 and/or GPU 204 to access, read, and/or execute one or more one or more algorithms, instructions, programs, applications, code, etc., stored in hold-release module 212 and/or BCI processing and testing module 214.

In various embodiments, BCI processing and testing module 214 may be configured to store one or more algorithms, instructions, programs, applications, code, etc., that are executed by CPU 202 and/or GPU 204 as part of an overall framework process. In some embodiments, this framework process includes the data processing instructions in accordance with a particular type of BCI. For example, when a test is administered to a user in a BCI format, the brain activity data signals for that user may be processed and analyzed in accordance with one or more types of BCI protocols. In various embodiments, BCI processing and testing module 214 may be configured to store instructions regarding this formatting, and how to process signals received from a brain activity monitoring system in accordance with one or more formats to interpret the user's intentions, selections, and/or decisions as the user is exposed to various stimuli.

For example, as previously discussed with reference to FIG. 1, various embodiments include BCI device 200 executing a three-step process for each test question to ensure that the user's selected answer is accurate. During each of these steps, BCI device 200 may cause images to be displayed to a user, via GPU 204, and to receive, via communication unit 206, data signals from a brain activity monitoring system in response to the user viewing stimuli associated with these images.

In an embodiment, BCI processing and testing module 214 may be configured to store instructions including the type of stimuli and/or images sent to display 206 and how CPU 202 processes signals received from a brain activity monitoring system in response to the user viewing these stimuli and/or images. For example, if a user's intention is determined in step one of the three-step process via an asynchronous BCI process, then BCI processing and testing module 214 may be configured to store instructions read by CPU 202 to process received brain activity signals in accordance with that asynchronous BCI process.

To provide another example, embodiments include the second step in the testing process determining a user's answer selection. Several types of brain activity processes may be implemented to facilitate this determination. For example, if steady-state visually evoked potentials (SSVEP) are implemented, GPU 204 may send images representative of test answers to a display (e.g., display 106). Based on the feedback received from data signals indicative of the user's brain activity, BCI processing and testing module 214 may include instructions regarding how to process this feedback in accordance with the SSVEP process to identify the displayed image that the user intends as an answer and/or to modify the displayed images to indicate the user's selected answer.

Furthermore, in various embodiments, BCI processing and testing module 214 may be configured to store instructions including the test questions, answer keys, user answers, and/or images representative of the test questions themselves. In various embodiments, BCI processing and testing module 214 may store any suitable number of tests, which may be administered when selected by an operator, such as by medical staff administering the test, for example. In various embodiments, an operator (e.g., medical staff member) may alter the contents of BCI processing and testing module 214 by uploading new tests and/or downloading test answers.

In an embodiment, BCI processing and testing module 214 may be configured to store instructions enabling CPU 202 to store a user's selected answers for any suitable number of test questions as a test answer profile. In an embodiment, the test profile may be generated by CPU 202 after the three-step process is applied to each test question. For example, the test answer profile could be an answer profile that conforms to a standard test key grading system, such as a listing of multiple-choice answers for each test question. In this way, once a standardized test is administered via BCI device 200, the answers to that test may be graded in accordance with the standard test answer key, greatly reducing grading errors that could otherwise be introduced when adapting the test for compatibility with the BCI test procedure.

In various embodiments, hold-release module 212 may be configured to store one or more algorithms, instructions, programs, applications, code, etc., that are executed by CPU 202 and/or GPU 204 to facilitate hold-release functionality, which will be further discussed below with reference to FIGS. 3A-B. For example, hold-release module 212 may include executable code in any suitable language and/or format. In some embodiments, hold-release module 212 may be configured to include instructions that are executed in conjunction with the third step in the three-step process that is applied during one or more questions for the administration of a cognitive test assessment, as previously discussed with respect to FIG. 1.

In other embodiments, hold-release module 212 may be configured to include instructions that are executed in conjunction with a hold and release control state change and may be used alternatively or in addition to a testing process. Again, further details regarding implementing the hold and release process for identifying and/or controlling state changes are discussed below with respect to FIGS. 3A-B.

Although FIG. 2 illustrates communication unit 206, CPU 202, GPU 204, and memory 208 as separate elements, various embodiments of BCI device 200 include any portion of communication unit 206, CPU 202, GPU 204, and memory 208 being combined, integrated, and/or separate from one another. For example, any of communication unit 206, CPU 202, GPU 204, and memory 208 could be integrated as a single device, a system on a chip (SoC), an application specific integrated circuit (ASIC), etc.

Furthermore, although data read/write module 210, hold-release module 212, and BCI processing and testing module 214 are illustrated as separate portions of memory 208, various embodiments include these memory modules being stored in any suitable portion of memory 208, in a memory implemented as part of CPU 202 and/or GPU 204, and/or spread across more than one memory. For example, data read/write module 208 could be stored as part of memory 208, while hold-release module 212 and BCI processing and testing module 214 are stored in a memory integrated as a part of CPU 202. As will be appreciated by those of ordinary skill in the relevant art(s), different memory modules may be integrated as a part of CPU 202 to increase processing speed, reduce latency and/or delays due to data processing bottlenecks, etc. For purposes of brevity, only a single memory 208 is illustrated in FIG. 2.

Although illustrated as a single BCI device in FIG. 2, in various embodiments BCI device 200 may consist of any number or group of one or more BCI devices. In accordance with such embodiments, each BCI device may include one or more CPUs and be configured to operate independently of the other BCI devices. BCI devices operating as a group may process signals received from a brain activity monitoring system individually (e.g., based on their availability) and/or concurrently (e.g., parallel processing).

Figure 3A:
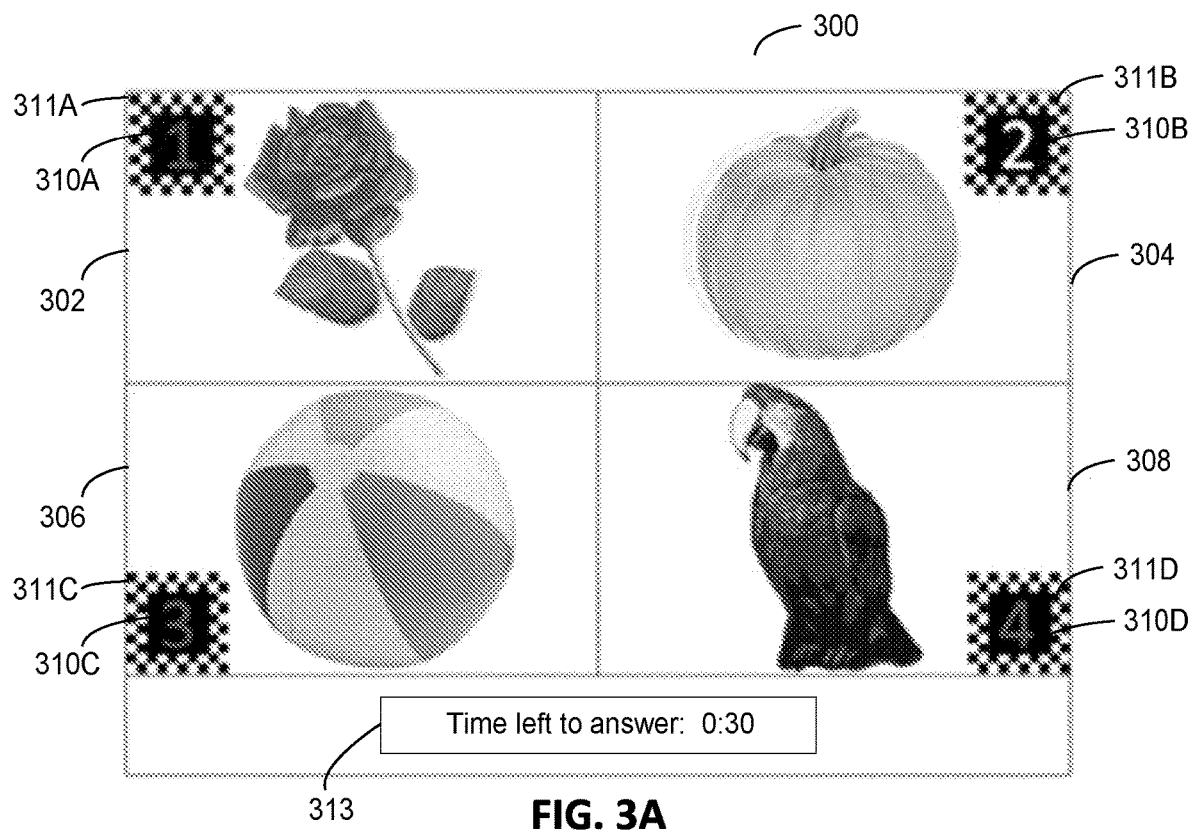
FIG. 3A illustrates an example of a test question image prior to a user making an answer selection, in accordance with an exemplary embodiment of the present disclosure.

FIG. 3A illustrates an example of a test question image 300 prior to a user making an answer selection, in accordance with an exemplary embodiment of the present disclosure. Test question image 300 includes four multiple-choice answer selections 302, 304, 306, and 308. Each of the four multiple-choice answer selections 302, 304, 306, and 308 also has an associated label 310A-D, respectively. Although FIG. 3A illustrates labels 310A-D as numbers 1-4, respectively, any suitable type of identifier may be used as labels 310A-D, such as letters, for example.

As shown in FIG. 3A, each of labels 310A-D is surrounded by a respective border pattern 311A-D, which may include a black and white checkerboard pattern, for example. In accordance with various embodiments, the black and white checkerboard patterns constituting each border pattern alternate patterns of black and white to "flicker" at a corresponding frequency. Several BCI methods are typically used to determine a user's decisions when exposed to these types of visual stimuli.

For example, using one type of BCI method, SSVEP, each of border patterns 311A-D may flicker at a different frequency than one another, and these frequencies may be high enough such that the flicker is not consciously counted by the user viewing the images. Nonetheless, the flicker frequency is able to be identified via an analysis of the user's brain activity data signals received at a BCI, such as BCI device 200, for example, while a user is viewing a selected answer image and its associated border pattern and label.

Although FIG. 3A illustrates each of border patterns 311A-D as having a black and white checkerboard pattern, any suitable pattern type may be used for border patterns 311A-D. For example, border patterns 311A-D may be implemented as having any suitable type of color, pattern, design, etc., which may be used to provide suitable SSVEP stimuli. For example, border patterns 311A-D may include a solid, single color that flickers at a particular frequency.

In another type of BCI method, P300, or event-related potential (ERP) BCI, each of labels 310A-D may flash at a slower rate, which may be counted by the user, and an analysis of the user's brain activity data signals received at a BCI, such as BCI device 200, for example, may indicate a positive change in the user's brain activity data signals about 300 milliseconds after each flash occurs. Identification of this positive change, whose timing may be specified for individual users, allows for the identification of the answer selection that the user intends to choose corresponding to each of respective labels 310A-D. Additionally or alternatively, various embodiments include any suitable portion of images 302, 304, 306, and 308 flashing, such as the images themselves.

Although FIG. 3A illustrates several labels 310A-D and their corresponding border patterns, embodiments include images 302, 304, 306, and 308 flickering in accordance with SSVEP frequencies or flashing in accordance with a P300 flash pattern. In accordance with such embodiments, labels 310A-D (and border patterns 311A-D) may be omitted and user 102 may be instructed, for example, that each test answer position corresponds to one of answers A-D for the duration of the test.

In various embodiments, each of border patterns 311A-D may flicker in accordance with SSVEP frequencies, each of labels 310A-D may flash in accordance with a P300 flash pattern, each of images 302, 304, 306, and 308 may flicker in accordance with SSVEP frequencies or flash in accordance with a P300 flash pattern, or any combination of flickering and/or flashing may occur among each of border patterns 311A-D, labels 310A-D, and/or images 302, 304, 306, and 308 may happen simultaneously.

For example, in an embodiment, border patterns 311A-D may flicker at a SSVEP frequency to allow BCI device 200 to process a user's brain activity data signals to assess the flicker frequency with a desired answer selection, while labels 310A-D may flash at the same time in accordance with a P300 flash pattern, additionally registering the user's recognition response to making the desired selection in accordance with a P300 BCI process.

Various embodiments of BCI device 200 may be implemented for the administration of any suitable test. However, the example image 300 shown in FIGS. 3A-B may correspond to one or more images such as those used in a PEABODY PICTURE VOCABULARY TEST—4$^{TH}$ EDITION (PPTV-IV), for example. The PPTV-IV test includes an oral pronunciation of a word, and allows a user to select the image that most closely resembles that word. For purposes of explanation, assume that "bird" is the correct answer to a test question represented by example image 308.

When a test is administered in accordance with various embodiments, the user would focus on label 310D and its corresponding border pattern 311D that are associated with image 308 to select this answer. In an embodiment, the three-step process may be applied to determine the user's selected answer.

As previously discussed, the first step in the three-step process is ascertaining whether a user is paying attention to the displayed answers or intends to answer the test question. In accordance with such an embodiment, FIG. 3A is an example of what may be displayed to a user during the first and second steps of such a three-step process. For example, if a timer is used to verify that a user is ready to decide upon an answer, timer 313 may be displayed indicating that the test has begun and a remaining time for the user to select an answer. To provide another example, a tone or other notification may be used to indicate a timer has started, which may or may not be visible to the user while the user prepares to make a decision.

In an embodiment, the second step may begin once timer 313 has started (or until an asynchronous BCI process, for example, otherwise indicates that the user intends to answer, until a threshold amount of time is left on the timer, etc.). That is, each respective answer selection's border pattern 311 and/or label 310 may being flickering before timer 313 starts, but BCI device 200 may wait until a determination that the user actually intends to answer before processing the user's brain activity data signals. Based on a monitoring of the user's brain activity data signals, BCI device 200 may then determine the user's selected answer, such as the answer associated with image 308, for example. Once BCI device 200 determines that the user has selected the answer associated with image 308, the image is modified to the image that is shown in FIG. 3B, which is further discussed below. By waiting until it is determined that the user intends to select an answer in this way, embodiments of BCI device 200 help to ensure that the answer determined during the second step is correct.

Figure 3B:
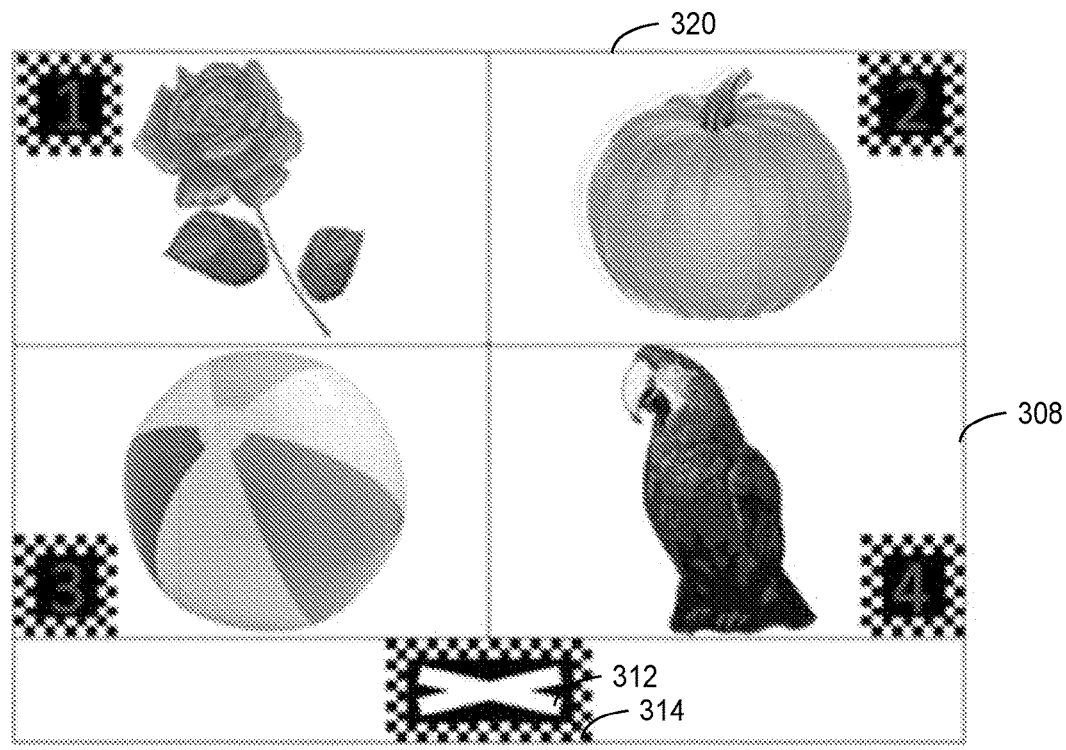
FIG. 3B illustrates an example of a test question image 320 used to verify a user's answer after BCI device 200 determines a user's answer selection, in accordance with an exemplary embodiment of the present disclosure.

FIG. 3B illustrates an example of a test question image 320 used to verify a user's answer after BCI device 200 determines a user's answer selection, in accordance with an exemplary embodiment of the present disclosure. In an embodiment, image 320, as shown in FIG. 3B, is shown to a user in accordance with the third step in the three-step answer selection process. That is, once a determination has been made by BCI device 200 that the user has selected answer image 308 from FIG. 3A, answer image 308 is maintained while the remaining images 302, 304, and 306 are de-emphasized in FIG. 3B. In various embodiments, this de-emphasizing may be implemented by any suitable methods such as fading, muting, removing, reducing, adjusting colors, etc., associated with the non-selected answer images.

In addition to the de-emphasis of the other answer images, embodiments also include the presentation of a cancellation image, an example of which is shown in FIG. 3B as cancellation image 312. Based on the particular BCI method used (e.g., P300, SSVEP, or both) cancellation image 312 may also include a border pattern 314. Similar to labels 310A-310D and border patterns 311A-D, cancellation image 312 and/or border pattern 314 may flicker at a specific SSVEP frequency and/or flash in accordance with a P300 flash pattern (e.g., as a sequence of stimuli that is part of a P300 flash sequence to illicit a P300 ERP). For example, cancellation image 312 may flash in accordance with a particular P300 flash pattern, border pattern 314 may flicker at a particular SSVEP frequency, or both.

Similar to border patterns 311A-D, various embodiments include border pattern 314 implemented as any suitable type of color, pattern, design, etc., which may be used to provide a suitable SSVEP stimuli. Once the user is presented with the image as shown in FIG. 3B, the user has two options. If the user intends to keep the selected answer corresponding to image 308, the user can maintain her focus on image 308. But if the user accidentally chose image 308 as the wrong selection (or if BCI device 200 misinterpreted the user's selection) then the user may switch her concentration to image 312 to cancel this selection. In accordance with various embodiments, BCI device 200 may be configured to detect whether the user intends to hold the selected answer image 308 or to change (i.e., release) from the holding state by focusing on cancellation image 312.

In an embodiment, BCI device 200 may be configured to present any suitable number of images (e.g., four, as in FIGS. 3A-3B) corresponding to the next test question if a holding state is detected, i.e., if BCI device 200 detects that the user is maintaining focus on image 308. Further in accordance with such an embodiment, BCI device 200 may be configured to replace FIG. 3B with the image shown in FIG. 3A if a release state is detected, i.e., if BCI device 200 detects that the user has switched his focus from image 308 to cancellation image 312.

In an embodiment, this process may be repeated any suitable number of times for each test question until an answer is obtained for all questions in the test. Once the test answers are collected, BCI device 200 may build and/or format a corresponding answer profile for the user that may be graded in accordance with a test answer key. For example, since each answer image has a corresponding number, test answers may be collected by identifying the answer images by number. For the previous example, once the user's selection of answer image 308 was verified, the answer number "4" may be recorded for that test question.

In various embodiments, the hold-release state transition detection may be implemented in a number of sub-steps as part of the third step in the three-step answer selection process. In an embodiment, training data may be collected for a particular user prior to running the test (or other system in which BCI device 200 is implemented). For example, the determination made by BCI device 200 regarding a user's particular selection is based upon the user's brain activity data signals, but is typically not an absolute certainty; rather, the decisions are typically performed in the context of a mathematical analysis.

In other words, because each user's brain activity is unique and difficult to measure, embodiments include BCI device 200 determining a user's selections by weighting the importance of portions of the brain activity data signals considered most highly correlated with the decision. For example, weights for individual portions of the brain activity data signals may be determined based on the classification of collected brain signal activity in response to a user being exposed to a particular set of known stimuli. These user may be exposed to the known stimuli through the training process, for example. The weights may be calculated via a classification process, resulting in a range of classifier values corresponding to each type of stimuli for SSVEP, to the presence or absence of evoked potentials such as the P300 ERP, etc.

For example, a selection classifier training process may be implemented for a particular user before a test is administered. The selection classifier training may correspond to the user viewing and/or concentrating on several different stimuli (e.g., border portions 311A-D) that flicker at various frequencies. Based on this training data, different ranges of classifier values may be calculated by BCI device 200 based on a user's brain activity while the user is exposed to different stimuli.

Once the selection classifier training process has been completed, BCI device 200 may calculate new (i.e., post-training) classifier values based upon the user's brain activity data signals during subsequent exposures to the same stimuli. These new classifier values may be compared to the different ranges of classifier values calculated during the selection classifier training process, to one another, and/or to one or more threshold values, which is further discussed below, to identify which of the subsequent stimuli the user is being exposed to (e.g., which image the user is focusing on). The various stimuli may correspond to one or more answer selections, actions, etc. Through an analysis of the user's brain activity data and updated classifier values, embodiments include BCI device 200 determining the user's decision to either hold the selected answer or to release the answer (i.e., cancel it).

In various embodiments, any suitable number of rules may be constructed to ensure that the user's decisions are accurately determined. For example, after the training data has been collected, BCI device 200 may continue to monitor the user's brain activity (i.e., receive and process the user's EEG data signals) while the user focuses on a particular stimuli after a selection has been made. This could include, for example, a user continuing to focus on stimuli provided by label 311B and border portion 310B of answer image 308, or switching his focus to border portion 314 associated with cancellation image 312, as shown in FIG. 3B. In an embodiment, BCI device 200 may be configured to generate another, subsequent classifier—a hold-release classifier, based on a comparison between (1) classifier values calculated during the monitoring of the user's brain activity after the user has made a selection, and (2) the range of hold-release classifier values that have been determined prior to testing, which may be referred to as "training classifier values," throughout this disclosure.

To provide an illustrative example, BCI device 200 may first calculate two threshold classifier values that separate the training classifier values associated with the user viewing a target stimulus and the classifier values associate with the user viewing an irrelevant stimulus. Continuing this example, during the selection classifier training process, a user may be instructed to consider one image (e.g., 308) as the correct answer from a set of images (target stimulus). The user may also be instructed to focus on cancellation image 314 (cancellation stimulus). Flashes of this image's respective label 310B and/or flickering of its border portion 311B would then be considered the target stimuli, while flashes of cancellation image 312 and/or flickering of border 314 would be considered the cancellation stimuli.

During the training process, the user's brain activity in response to the target and cancellation stimuli may be used to calculate weights for a classifier in accordance with any suitable classification method, such as a least squares regression analysis, for example. Application of these weights to an individual's brain activity data signals would produce classifier values. As a result of the selection classifier training process, one range of classifier values would be identified as associated with the target stimuli while another range of classifier values would be associated with non-relevant stimuli.

In an embodiment, thresholds at the border of these ranges may be used as an indication of whether a new classifier value (e.g., from subsequent exposure to either target or cancellation stimuli) should be considered to be the result of a user's exposure to a target stimuli, to a cancellation stimuli, or remain unknown. In various embodiments, a determination of an unknown response may be further analyzed with additional rules, as further discussed below, to determine whether the new classifier value should be considered to be in response to a user's exposure to a target or a cancellation stimuli.

Further expanding upon this exemplary rule, BCI 200 may identify various stimuli, from classifier values calculated using the user's brain activity data signals while exposed to the stimuli, based upon a comparison between the subsequently calculated classifier values and the corresponding range of target classifier values.

Furthermore, in accordance with an embodiment, BCI device 200 may use the largest classifier values to identify a target stimuli selection by the user. But since the hold-release decision with reference to FIG. 3B is only with regards to two possible choices, only classifier value ranges for the brain activity response to answer stimuli associated with image 308 and cancellation image 312 are required. That is, if the selection classifier training process resulted in the calculation of a range of classifier values corresponding to values designated as C1-C10 for a target stimuli selection by the user, and classifier value ranges designated as C20-C30 for cancellation stimuli selection by the user, the rule could set one or more threshold classifier values to separate the ranges (C1-C10) and (C20-C30).

Using this rule, a user's intention to hold the selected answer image 308 in FIG. 3B could be determined by BCI device 200 when the classification of the user's brain activity data signals results in a classifier value equal to or greater than a threshold classifier value (e.g., C15) such that classifier values falling above or below the one or more threshold values are associated with the user either continuing to focus to the target stimuli or switching to the cancellation stimuli. In various embodiments, any suitable threshold classifier value may be utilized, such as a threshold classifier at the lower end of C1-C10, a classifier threshold value at the upper end of C20-C30, zero, etc.

Another example of a rule may include comparing a classifier value calculated from the user's brain activity data signals during the third step with a predetermined classifier value. For example, if a classifier value associated with image 308 during the third step is a negative value (assuming zero was determined from the training process classifier values as a baseline below which classifier values are associated with cancellation stimuli) then BCI device 200 may determine that the user has decided to select cancellation image 312 instead of answer image 308. In other words, in this rule example, a negative classifier value indicates a negative correlation to a user's intention to hold the selected answer image 308, and therefore the hold state is switched to cancellation image 312.

When implementing such a rule, BCI device 200 may determine, for example, if one or more conditions are met, and identify the user's decision (i.e., the appropriate holding state) based on any suitable combination of these conditions being satisfied. For example, BCI device 200 may implement a three-part rule. An example of the three-part rule could include BCI device 200 first determining which of the two classifier values is larger than the other. Using a typical classifier system, a higher classifier value is typically associated with a higher correlation between the user's decisions to hold one state (e.g., the selected image 308) versus another state (e.g., cancellation image 312). Second, BCI device 200 may then determine whether the first and second classifier values are both positive, which could indicate a better correlation between the user intending to select either one of the states. Third, BCI device 200 may determine whether the first and second classifier values are both less than a threshold value, such as the threshold value as previously discussed with respect to the first rule, for example. If all three rule conditions are satisfied in the example third rule, BCI device 200 may identify the state associated with the higher classifier value as the holding state.

Furthermore, although the hold and release process has been described in terms of a single hold and a single release state mapped to individual control states, various embodiments include any suitable combination of various hold and/or release states. For example, a user could be exposed to any number of stimuli associated with respective holding states and a single release state that stops the activity associated with the currently selected holding state. Such embodiments could be particularly useful when, for example, it is desirable to provide a user with access to multiple holding states that may be used to provide more complex types of control, such as turning, increasing speed, decreasing speed, etc., that form part of a singularly controlled device.

Although the details of the hold-release concept have been explained with reference to a user selecting answers to test questions, embodiments include BCI device 200 implementing the hold-release functionality as part of any suitable system that utilizes state changes. That is, a holding state may be identified with any state the user wishes to maintain, while the release state may be associated with any state that results from the user's desire to stop the holding state.

To provide another example, the hold and release states could be applied to motor controls for a motor-powered wheelchair, or any other suitable type of motored assisting device. In such an embodiment, the holding state could be associated with a forward movement or a turn, while the release state could be associated with the stoppage of the movement or turn. In addition, embodiments include the hold and release states switching their associated mapped control behaviors for a particular application. As previously discussed, the detection and switching of the identification of hold and release states could be especially useful in such embodiments. That is, a user may wish to quickly switch between moving forward, stopping, and then moving forward again. In such an example, embodiments include the holding state initially being identified as the movement state and the release state initially being identified as the stopping state. Once the user decides to stop his movement, the holding state could then be identified as the stopped state, and the released state identified as the movement state. In an embodiment, these states could continuously switch to allow a user's desired decisions to be interpreted quickly and accurately.

In yet another example, the hold-release states could be applied to any suitable type of speller used to provide or supplement an impaired user's speech. In such an embodiments, any suitable number of hold and release states could be associated with any suitable number of locations, rows, columns, etc., of a BCI speller. The hold and release system could be implemented in the context of a BCI speller by interpreting a user's intention to select one or more locations with a holding state, and providing a cancelation image to release the selection in the case of an erroneous selection, interpreting continued attention to the location as a hold and confirmation.

Figure 4:
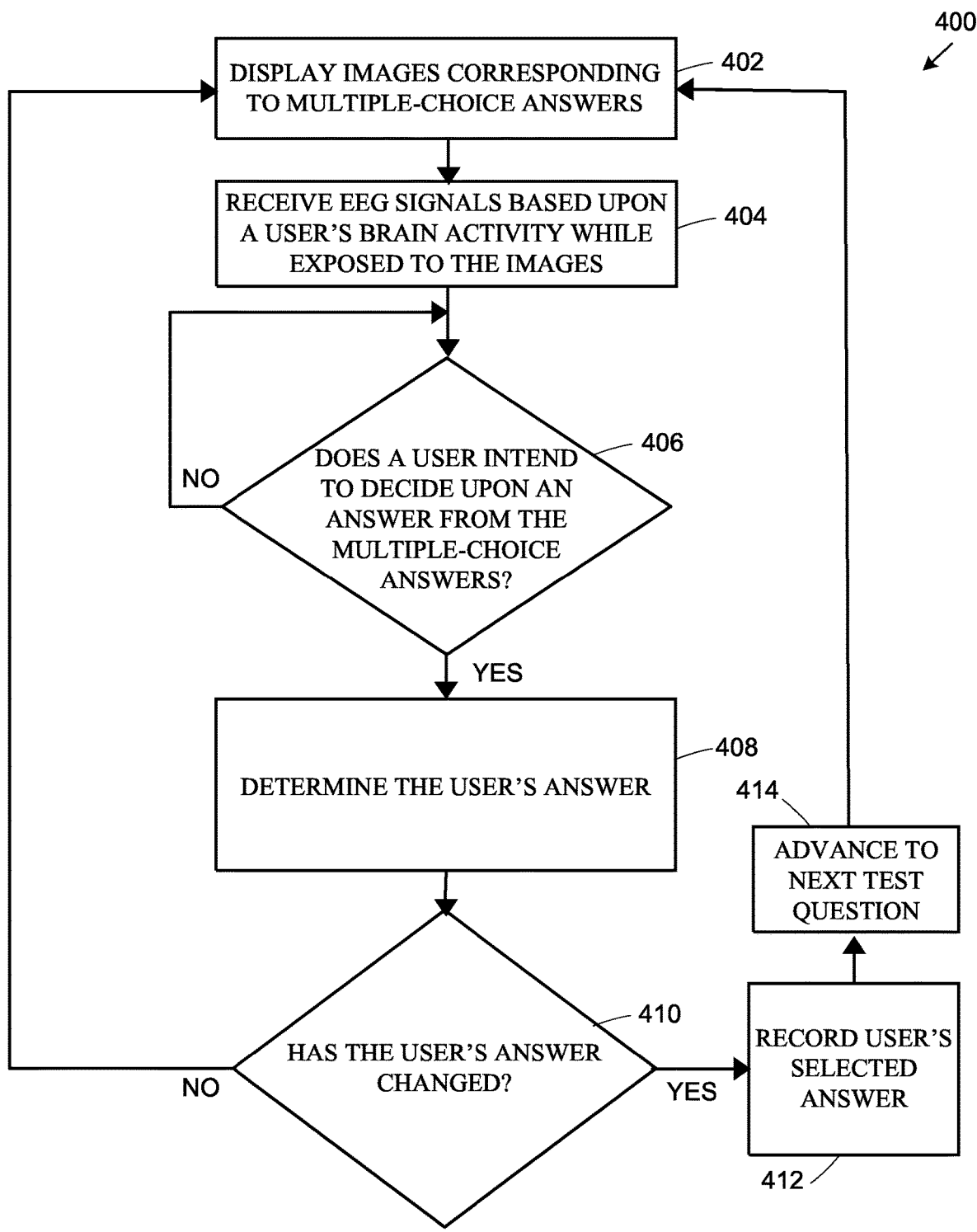
FIG. 4 illustrates an example test answer selection method 400 in accordance with an exemplary embodiment of the present disclosure.

FIG. 4 illustrates an example test answer selection method 400 in accordance with an exemplary embodiment of the present disclosure. In the present embodiment, method 400 may be implemented by any suitable computing device (e.g., BCI device 104 or BCI device 200, as shown in FIGS. 1 and 2, respectively). In one aspect, method 400 may be performed by one or more algorithms, instructions, programs, applications, code, etc., such as any suitable portion of CPU 202 executing instructions in one or more of the modules stored in memory 208, for example, as shown in FIG. 2.

Method 400 may begin when one or more processors display images corresponding to multiple-choice answers for the cognitive assessment test (block 402). This may include, for example, displaying images in accordance with a standardized test format, such as a standardized cognitive assessment test used to measure a user's cognitive abilities, in an embodiment (block 402). In an embodiment, the images may be generated, for example, by one or more GPUs of a BCI device, such as GPU 204, as shown in FIG. 2, for example. The images may include, for example, images corresponding to the images shown in FIG. 3A that are retrieved from CPU 202 and/or GPU 204 from one or more portions of memory 208, which could include retrieval of one or more saved files from BCI processing and testing module 214, for example (block 402).

Method 400 may include one or more processors receiving EEG signals based upon a user's brain activity during administration of a cognitive assessment test (block 404). The EEG signals may be generated, for example, via any suitable brain activity monitoring system configured to measure the user's brain activity, such as brain activity monitoring system 103, for example, as shown in FIG. 1 (block 404).

Method 400 may include one or more processors determining whether a user intends to decide upon an answer from the multiple-choice answers (block 406). This determination could be made, for example, by one or more CPUs of a BCI device, such as CPU 202, as shown in FIG. 2, for example, in an embodiment (block 406). For example, this determination may be made when one or more processors display a timer to inform a user to decide upon an answer before time runs out, such as timer 313, for example, as shown in FIG. 3A (block 406). To provide another example, this determination may be made via an asynchronous BCI process performed on the user's EEG signals (block 406) while taking the test.

If the one or more processors determine that the user is ready to decide upon an answer, method 400 proceeds to determine the user's answer (block 408). Otherwise, method 400 continues to wait for the user to be ready to decide upon a displayed answer image (block 406). In an embodiment, the determination of whether the user is ready to decide upon an answer corresponds to the first step in a three-step answer selection and verification process (block 406).

Method 400 may include one or more processors determining the user's selection from the multiple-choice answers (block 408). In an embodiment, the determination of the user's selection is part of a second step in a three-step answer selection and verification process (block 408). This determination may include, for example, monitoring the user's brain activity data signals (e.g., EEG signals) in response to the user being presented with the displayed images (block 402) in accordance with an SSVEP BCI and/or a P300 BCI process, in various embodiments (block 408).

Method 400 may include one or more processors determining whether the user's answer (block 408) has changed (block 410). This may include, for example, one or more processors continuing to receive EEG signals from the user after the determination of the user's selected answer (block 408) to verify whether the user's brain activity indicates a match to the user's previously selected answer (block 410). In an embodiment, the verification of the user's answer (block 408) is part of a third step in a three-step answer selection and verification process (block 410).

In the present embodiment, method 400 may include verifying the user's answer (block 408) by one or more processors modifying the displayed images (block 402) to de-emphasize other answer selections while presenting a cancellation image, as shown in FIG. 3B (block 410). This may also include, for example, one or more processors processing the user's brain activity to determine whether the user's selected answer corresponds to a current holding state, or whether the user's brain activity indicates the user's intention to cancel the selected answer through the identification of a release state associate with the user's focus on the cancellation image (block 410). If the user's selected answer is verified and/or the release state is not detected, method 400 continues to record the user's selected answer (block 410). Otherwise, method 400 reverts back to displaying the initial images presented to the user prior to the user making the selection (block 402).

Method 400 may include one or more processors recording the user's answer (block 412). This may include, for example, one or more processors, such as CPU 202 as shown in FIG. 2, for example, storing the user's verified selected answer (block 410) in a memory, such as memory 208, for example, in an embodiment (block 412).

Method 400 may include one or more processors advancing to the next test question (block 414). This may include, for example, one or more processors, such as CPU 202 as shown in FIG. 2, for example, retrieving the next test question from testing and processing module 214 of memory 208, for example, in an embodiment (block 414). If the last test question was recorded, method 400 may include one or more processors formatting and/or storing the entire user answer profile in a memory, such as memory 208, as shown in FIG. 2, for example (block 414). Once the next test question is advanced at block 412, method 400 may include displaying the next test question to the user (block 402).

Figure 5:
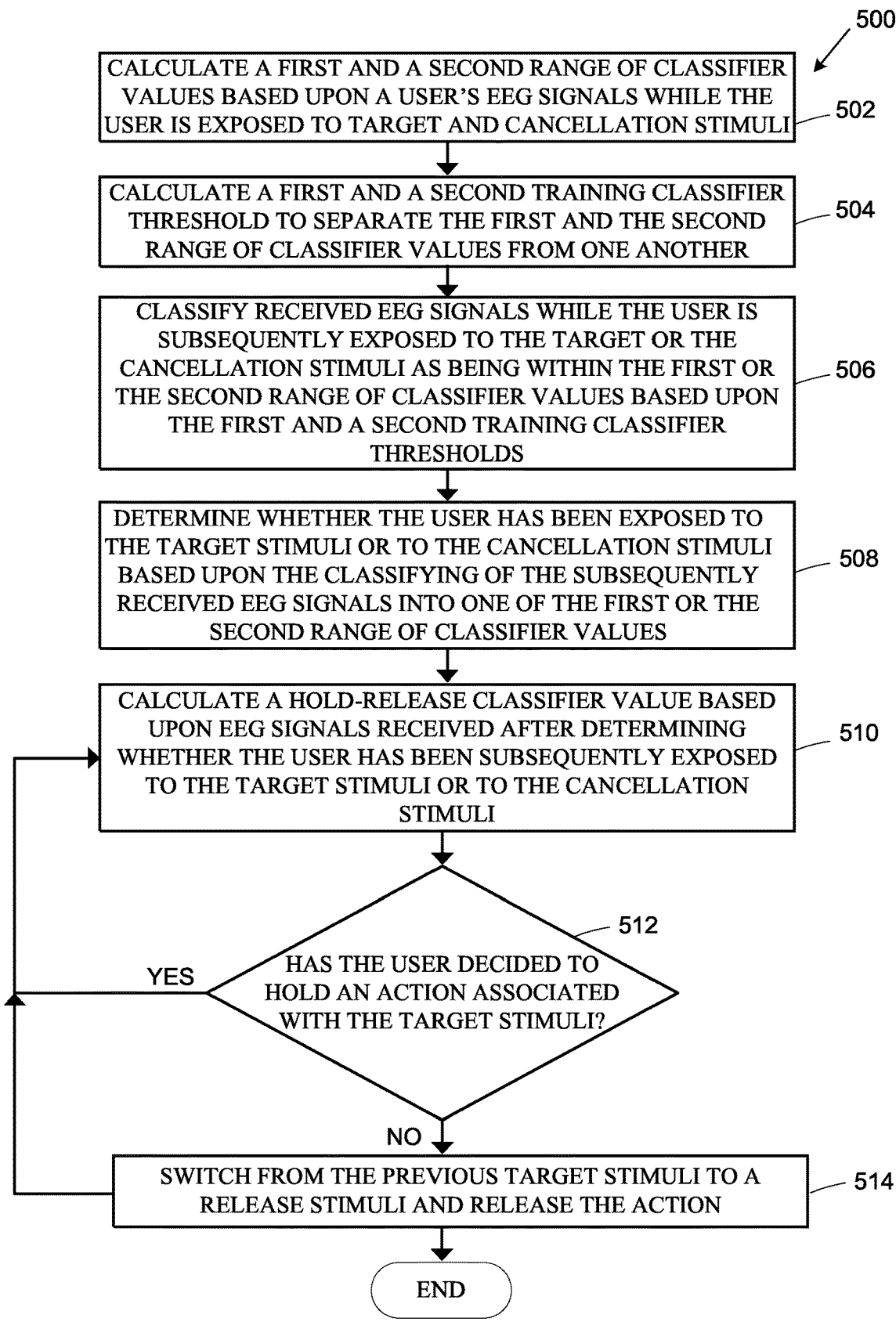
FIG. 5 illustrates an example hold-release state determination method 500 in accordance with an exemplary embodiment of the present disclosure.

FIG. 5 illustrates an example hold-release state determination method 500 in accordance with an exemplary embodiment of the present disclosure. In the present embodiment, method 500 may be implemented by any suitable computing device (e.g., BCI device 104 or BCI device 200, as shown in FIGS. 1 and 2, respectively). In one aspect, method 500 may be performed by one or more algorithms, instructions, programs, applications, code, etc., such as any suitable portion of CPU 202 executing instructions in one or more of the modules stored in memory 208, for example, as shown in FIG. 2. In an embodiment, method 500 is an implementation of the third verification step in a three-step process, as previously discussed with reference to FIG. 3B, for example.

Method 500 may begin when one or more processors calculate a first and a second range of classifier values based upon a user's EEG signals (block 502). In an embodiment, the first and second range of classifier values may be calculated based upon the user's exposure to target and cancellation stimuli, respectively (block 502).

For example, the first and a second range of classifier values may be calculated as training classifier values during a training session whereby the user is exposed to various stimuli that may be associated with various applications of a BCI, such as administration of a cognitive test, a speller, controls for a motor-powered wheelchair, etc. (block 502). For example, the first and second stimuli could include a user's exposure to stimuli associated with a selected test answer image and a cancellation image, such as a flickering borders 310A-D and/or border 314 as shown in FIG. 3B, respectively, in an embodiment.

Method 500 may include one or more processors calculating a first and a second training classifier threshold (block 504). In an embodiment, the first and second training classifier thresholds may be calculated based upon the first and the second range of classifier values, such that the first and second training classifier threshold separate the first and the second range of classifier values from one another (block 504).

Method 500 may include one or more processors classifying received EEG signals while the user is subsequently exposed to the target or the cancellation stimuli (block 506). This classification may include, for example, classifying the signals as being within the first or the second range of classifier values based upon the first and a second training classifier thresholds (block 506).

Method 500 may include one or more processors determining whether the user has been exposed to the target stimuli or to the cancellation stimuli based upon the classifying of the subsequently received EEG signals into one of the first or the second range of classifier values (block 508). This may include, for example, comparing the classified EEG signals corresponding to determine which of the first or the second range of classifier values the classified EEG signals fall within (block 508).

Method 500 may include one or more processors calculating a hold-release classifier value based upon EEG signals received after determining (block 508) whether the user has been subsequently exposed to the target stimuli or to the cancellation stimuli (block 510). The calculation may include, for example, classifying the user's brain activity (e.g., EEG signals) using any suitable techniques as previously discussed with respect to FIG. 3B to generate the hold-release classifier value (block 510).

Method 500 may include one or more processors identifying whether the user has decided to hold an action associated with the target stimuli, or to release the action by switching to the cancellation stimuli, based upon a comparison between the hold-release classifier value and the first and second training classifier thresholds (blocks 512 and 514).

That is, method 500 may include one or more processors comparing the calculated hold-release classifier value (block 510) to the calculated first and second training classifier thresholds (block 504) to determine whether the user has decide to hold an action associated with the target stimuli (block 512). In various embodiments, method 500 may include the identification of the hold and release states using any suitable combination of the three rules as previously discussed with reference to FIG. 3B, for example, to establish whether a selected test answer image (or any other suitable stimulus that may be implemented with the identification of hold and release states) should be held (kept) or released (cancelled) (block 512).

For example, the determination of whether the user has decided to hold the action associated with the original target stimuli may be determined (block 512) when the calculated hold-release classifier value (block 510) is greater than the first training classifier threshold (block 504).

To provide another example, the determination that the user has decided not to hold the action associated with the target stimuli may be determined (block 512) when the calculated hold-release classifier value (block 510) is less than the second training classifier threshold (block 504).

If it is determined that the user has decided to hold the action associated with the target stimuli (block 512), then method 500 reverts to continuing to receive EEG signals and calculating hold-release classifiers (block 510). If it is determined that the user has not decided to hold the action associated with the target stimuli (block 512), then method 500 continues (block 514).

In various embodiments, once the determination that the user has decided to hold the action associated with the original target stimuli is made, method 500 may include generating additional hold-release classifier values (block 510) based on the most recent brain activity monitoring and then comparing the new hold-release classifier value to a previously generated hold-release classifier and/or to the first and/or second classifier thresholds (block 512). In various embodiments, the comparisons of more than one hold-release classifier value may be implemented using any suitable number of rules as previously discussed with reference to FIG. 3B, for example.

Various embodiments include repeating the acts of calculating the hold release classifier value (block 510) and determining if the user has decided to hold the action associated with the target stimuli (block 512). In this way, method 500 may facilitate the continuous determination of whether to maintain the holding state or to switch to a release state (blocks 510 and 512).

Method 500 may include one or more processors identifying a switch from the previous target stimuli to a release stimuli to release the action represented by the hold state (block 514). This may include, for example, the determination that a user changed her concentration from one particular stimuli (e.g., flickering and/or flashing) associated with holding a presented test answer image (e.g., maintaining concentration on image 308) to another stimuli associated with the release of the identified holding state (e.g., switching concentration to cancellation image 312).

Once the switch is made from the previous target stimuli to a release stimuli (block 514), method 500 may revert back to calculating the hold release classifier value (block 510). But, when this is done, embodiments include the association of the hold state switching to the cancellation stimuli, and vice-versa.

To provide an illustrative example, a user may be initially exposed to a target stimuli (e.g., one presented with a test answer image) and this maintained exposure may be associated with the holding state. Method 500 may determine (block 512) that the user has intended to cancel the test question by switching his exposure from the target stimuli to the cancellation stimuli (cancellation image) (block 514). Once this occurs, the reversion to the calculation of the subsequent hold-release classifier value (block 510) results in the association of the original target stimuli (test question image) being switched to the cancellation stimuli (release state). This reversion also results in the association of the original cancellation stimuli (cancellation image) being switched to the target stimuli (hold state).

As a result, the release state is subsequently processed as the new hold state, and vice-versa. If, after the reversion (block 514 to block 510), the user switched his focus back to a test question, the calculated hold-release classifier value (block 510) would be used and the determination made that the user has not decided to hold the action associated with the cancellation image (block 512). This process may repeat, switching the hold and release states any suitable number of times until one or more conditions are met (end), which is further discussed below.

In some embodiments, the number of times this reversion process is repeated (blocks 510, 512, and 514) may be limited. For example, this reversion process may be repeated by monitoring the user's brain activity over a predetermined period of time, over a threshold maximum number of loops, etc., in which case method 500 may end. These embodiments may be particularly useful when a determination of whether the user has decided to hold the action associated with the original target stimuli needs to be made within a relatively short period of time, such as in a testing environment, for example. In this way, method 500 allows for brain activity to be monitored over several iterations to determine whether a holding state is maintained, thereby providing an accurate determination of the user's decisions.

In other embodiments, method 500 may continuously repeat the reversion process (blocks 510, 512, and 514) without necessarily ending. These embodiments may be particularly useful in implementations of a BCI used for control systems. For example, if the BCI was implemented as part of a motorized wheelchair, then it may be preferable to associate the holding state with moving the wheelchair forward, continuously monitoring the user's brain activity until a release state (or a safety stop) is detected.

Upon reading this disclosure, those of skill in the art will appreciate still additional alternative structural and functional designs for using a BCI and/or other suitable control interfaces through the disclosed principles herein. For example, although several embodiments have been provided throughout the disclosure relating to cognitive testing and wheelchair control implementations, various embodiments may include any suitable type of application utilizing state changes. To provide a specific example, a gaming application may be implemented utilizing the hold-release algorithms as discussed herein. The gaming application may present other suitable types of stimuli instead of test questions and cancellation images that are relevant to a particular gaming application The hold-release process, as discussed throughout the disclosure, may then be applied to determine whether the user is ready to select from among various presented stimuli, whether the user intends to maintain a selection, whether the user intends to cancel the selection, to switch the selection to another stimuli, etc.

Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter of the present disclosure.

Additionally, certain embodiments are described herein as including logic or a number of components or modules. Modules may constitute either software modules (e.g., code stored on a machine-readable medium) or hardware modules. A hardware module is tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In some cases, a hardware module may include dedicated circuitry or logic that is permanently configured (e.g., as a special-purpose processor, such as a field programmable gate array (FPGA) or an application-specific integrated circuit (ASIC)) to perform certain operations. A hardware module may also include programmable logic or circuitry (e.g., as encompassed within a general-purpose processor or other programmable processor) that is temporarily configured by software to perform certain operations. It will be appreciated that the decision to implement a hardware module in dedicated and permanently configured circuitry or in temporarily configured circuitry (e.g., configured by software) may be driven by cost and time considerations.

Accordingly, the term hardware should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware and software modules can provide information to, and receive information from, other hardware and/or software modules. Accordingly, the described hardware modules may be regarded as being communicatively coupled. Where multiple of such hardware or software modules exist contemporaneously, communications may be achieved through signal transmission (e.g., over appropriate circuits and buses) that connect the hardware or software modules. In embodiments in which multiple hardware modules or software are configured or instantiated at different times, communications between such hardware or software modules may be achieved, for example, through the storage and retrieval of information in memory structures to which the multiple hardware or software modules have access. For example, one hardware or software module may perform an operation and store the output of that operation in a memory device to which it is communicatively coupled. A further hardware or software module may then, at a later time, access the memory device to retrieve and process the stored output. Hardware and software modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a SaaS. For example, at least some of the operations may be performed by a group of computers (as examples of machines including processors), these operations being accessible via a network (e.g., the Internet) and via one or more appropriate interfaces (e.g., application program interfaces (APIs).)

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Some portions of this specification are presented in terms of algorithms or symbolic representations of operations on data stored as bits or binary digital signals within a machine memory (e.g., a computer memory). These algorithms or symbolic representations are examples of techniques used by those of ordinary skill in the data processing arts to convey the substance of their work to others skilled in the art. As used herein, an "algorithm" or a "routine" is a self-consistent sequence of operations or similar processing leading to a desired result. In this context, algorithms, routines and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, nonvolatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternate embodiments, using either current technology or technology developed after the filing date of this application.

The particular features, structures, or characteristics of any specific embodiment may be combined in any suitable manner and in any suitable combination with one or more other embodiments, including the use of selected features without corresponding use of other features. In addition, many modifications may be made to adapt a particular application, situation or material to the essential scope and spirit of the present invention. It is to be understood that other variations and modifications of the embodiments of the present invention described and illustrated herein are possible in light of the teachings herein and are to be considered part of the spirit and scope of the present invention. By way of example, and not limitation, the present disclosure contemplates at least the following aspects:

1. A computer-implemented method for determining answers to a cognitive assessment test, comprising:

displaying, by one or more processors, images corresponding to multiple-choice answers for the cognitive assessment test;

receiving, by one or more processors, electroencephalograph (EEG) signals based upon a user's brain activity during administration of the cognitive assessment test;

determining, by one or more processors, whether the user intends to decide upon an answer from the multiple-choice answers based upon the EEG signals;

determining, by one or more processors, the user's answer from the multiple-choice answers based upon the EEG signals after it is determined that the user intends to decide upon the answer; and verifying, by one or more processors, the user's answer based upon the EEG signals received after the user's answer has been determined.

2. The computer-implemented method of claim 1, wherein the acts of receiving the EEG signals, determining whether the user intends to decide upon an answer, determining the user's answer, and verifying the user's answer are performed without motor or oral feedback provided by the user.

3. The computer-implemented method of either claim 1 or claim 2, wherein the act of determining the user's answer comprises:

determining the user's answer based upon the EEG signals received in response to the user paying attention to an image from among the images corresponding to multiple-choice answers, and wherein the act of verifying the user's answer comprises:

verifying the user's answer based upon the EEG signals received in response to the user continuing to pay attention to the image after the user's answer has been determined.

4. The computer-implemented method of any one of claims 1-3, wherein the act of determining whether the user intends to decide upon an answer comprises:

determining that the user intends to decide upon an answer when a timer is displayed indicating a time period for the user to decide upon an answer.

5. The computer-implemented method of any one of claims 1-4, further comprising:

once the user's answer has been determined, modifying the images corresponding to the multiple-choice answers by maintaining the image of the determined answer while de-emphasizing images corresponding to the remaining answers; and generating a cancellation image indicative of an option to allow the user to cancel the determined answer when the user pays attention to the cancellation image, and wherein the act of verifying the user's answer comprises:

verifying the user's answer by determining whether the user is paying attention to the image of the selected answer or the cancellation image based on the received EEG signals.

6. The computer-implemented method of any one of claims 1-5, wherein the cognitive assessment test is a standardized test having a plurality of test questions, the answers to which provide a test answer profile, and further comprising:

repeating the acts of displaying images, receiving EEG signals, determining whether the user intends to decide upon an answer, determining the user's answer, and verifying the user's answer for each of the plurality of test questions to provide a user answer profile; and formatting the user answer profile in accordance with the test answer profile to facilitate grading of the standardized test.

7. A non-transitory, tangible computer-readable medium storing machine-readable instructions for determining answers to a cognitive assessment test that, when executed by a processor, cause the processor to:

display images corresponding to multiple-choice answers for the cognitive assessment test;

receive electroencephalograph (EEG) signals based upon a user's brain activity during administration of the cognitive assessment test;

determine whether the user intends to decide upon an answer from the multiple-choice answers based upon the EEG signals;

determine the user's answer from the multiple-choice answers based upon the EEG signals after it is determined that the user intends to decide upon the answer; and verify the user's answer based upon the EEG signals received after the user's answer has been determined.

8. The non-transitory, tangible computer-readable medium of claim 7, wherein the instructions to of receive the EEG signals, to determine whether the user intends to decide upon an answer, to determine the user's answer, and to verify the user's answer are executed by the processor without motor or oral feedback provided by the user.

9. The non-transitory, tangible computer-readable medium of either claim 7 or claim 8, wherein the instructions to determine the user's answer further include instructions that, when executed by the processor, cause the processor to:

determine the user's answer based upon the EEG signals received in response to the user paying attention to an image from among the images corresponding to multiple-choice answers, and wherein the instructions to verify the user's answer include instructions to:

verify the user's answer based upon the EEG signals received in response to the user continuing to pay attention to the image after the user's answer has been determined.

10. The non-transitory, tangible computer-readable medium of any one of claims 7-9, wherein the instructions to determine whether the user intends to decide upon an answer further include instructions that, when executed by the processor, cause the processor to:

determine that the user intends to decide upon an answer when a timer is displayed indicating a time period for the user to decide upon an answer.

11. The non-transitory, tangible computer-readable medium of any one of claims 7-10, further including instructions that, when executed by the processor, cause the processor to:

once the user's answer has been determined, to modify the images corresponding to the multiple-choice answers by maintaining the image of the determined answer while de-emphasizing images corresponding to the remaining answers; and generate a cancellation image indicative of an option to allow the user to cancel the determined answer when the user pays attention to the cancellation image, and wherein the instructions to verify the user's answer include instructions to:

verify the user's answer by determining whether the user is paying attention to the image of the selected answer or the cancellation image based on the received EEG signals.

12. The non-transitory, tangible computer-readable medium of any one of claims 7-11, wherein the cognitive assessment test is a standardized test having a plurality of test questions, the answers to which providing a test answer profile, further including instructions that, when executed by the processor, cause the processor to:

repeat the execution of instructions to display images, receive EEG signals, determine whether the user intends to decide upon an answer, determine the user's answer, and verify the user's answer for each of the plurality of test questions to provide a user answer profile; and format the user answer profile in accordance with the test answer profile to facilitate grading of the standardized test.

13. A method implemented in a brain-computer interface (BCI) computer, comprising:

calculating, by one or more processors, a first and a second range of classifier values based upon a user's electroencephalograph (EEG) signals while the user is exposed to a target and to a cancellation stimuli, respectively;

calculating, by one or more processors, a first and a second training classifier threshold to separate the first and the second range of classifier values from one another;

classifying, by one or more processors, received EEG signals while the user is subsequently exposed to the target or the cancellation stimuli as being within the first or the second range of classifier values based upon the first and a second training classifier thresholds;

determining, by one or more processors, whether the user has been exposed to the target stimuli or to the cancellation stimuli based upon the classifying of the subsequently received EEG signals into one of the first or the second range of classifier values;

calculating, by one or more processors, a hold-release classifier value based upon EEG signals received after determining whether the user has been subsequently exposed to the target stimuli or to the cancellation stimuli; and identifying, by one or more processors, whether the user has decided to hold an action associated with the target stimuli or to release the action by switching to the cancellation stimuli based on a comparison between the hold-release classifier value and the first and second training classifier thresholds.

14. The method of claim 13, further comprising:
executing, by one or more processors, one or more actions when it is determined that the user has decided to hold the action associated with the target stimuli; and stopping, by one or more processors, the execution of one or more actions when it is determined that the user has decided to release the action by switching to the cancellation stimuli.

15. The method of any one of claims 13-14, wherein the act of identifying whether the user decides to hold the action comprises:
identifying the user's decision to hold the action associated with the target stimuli when the hold-release classifier value is greater than the first training classifier threshold.

16. The method of any one of claims 13-15, wherein the act of identifying whether the user decides to release the action comprises:
identifying a user's decision to release the action associated with the target stimuli when the hold-release classifier value is less than the second training classifier threshold.

17. The method of any one of claims 13-16, further comprising:
generating an additional hold-release classifier value based upon EEG signals received after the determination that the user has decided to hold the action associated with the target stimuli; and determining that the user has decided to hold the action associated with the target stimuli when:
the hold-release classifier value is greater than the additional hold-release classifier value;
the hold-release classifier value and the additional hold-release classifier value are both positive; and
the hold-release classifier value and the additional hold-release classifier value are both less than the first training classifier threshold.

18. A non-transitory, tangible computer-readable medium storing machine-readable instructions for determining answers to a cognitive assessment test that, when executed by a processor, cause the processor to:
calculate a first and a second range of classifier values based upon a user's electroencephalograph (EEG) signals while the user is exposed to target and cancellation stimuli, respectively;
calculate a first and a second training classifier threshold to separate the first and the second range of classifier values from one another;
classify received EEG signals while the user is subsequently exposed to the target or the cancellation stimuli as being within the first or the second range of classifier values based upon the first and a second training classifier thresholds;
determine whether the user has been exposed to the target stimuli or to the cancellation stimuli based upon the classifying of the subsequently received EEG signals into one of the first or the second range of classifier values;

calculate a hold-release classifier value based upon EEG signals received after determining whether the user has been subsequently exposed to the target stimuli or to the cancellation stimuli; and identify whether the user has decided to hold an action associated with the target stimuli or to release the action by switching to the cancellation stimuli based on a comparison between the hold-release classifier value and the first and second training classifier thresholds.

19. The non-transitory, tangible computer-readable medium of claim 18, further including instructions that, when executed by the processor, cause the processor to:
execute one or more actions when it is determined that the user has decided to hold the action associated with the target stimuli; and stop the execution of one or more actions when it is determined that the user has decided to release the action by switching to the cancellation stimuli.

20. The non-transitory, tangible computer-readable medium of any of claims 18-19, wherein the instructions to identify whether the user decides to hold the selected action further include instructions that, when executed by the processor, cause the processor to:
identify the user's decision to hold the action associated with the target stimuli when the hold-release classifier value is greater than the first training classifier threshold.

21. The non-transitory, tangible computer-readable medium of any of claims 18-20, wherein the instructions to identify whether the user decides to release the selected action further include instructions that, when executed by the processor, cause the processor to:
identify a user's decision to release the action associated with the target stimuli when the hold-release classifier value is less than the second training classifier threshold.

22. The non-transitory, tangible computer-readable medium of any of claims 18-21, further including instructions that, when executed by the processor, cause the processor to:
generate an additional hold-release classifier value based upon EEG signals received after the determination that the user has decided to hold the action associated with the target stimuli; and determine that the user has decided to hold the action associated with the target stimuli when:
the hold-release classifier value is greater than the additional hold-release classifier value;
the hold-release classifier value and the additional hold-release classifier value are both positive; and
the hold-release classifier value and the additional hold-release classifier value are both less than the first training classifier threshold.

What is claimed is:

1. A method implemented in a brain-computer interface (BCI) computer, the method comprising:
calculating, by one or more processors, a first and a second range of classifier values based upon a user's electroencephalograph (EEG) signals while the user is exposed to a target and to a cancellation stimuli, respectively;
calculating, by one or more processors, a first and a second training classifier threshold to separate the first and the second range of classifier values from one another;
classifying, by one or more processors, received EEG signals while the user is subsequently exposed to the target or the cancellation stimuli as being within the first or the second range of classifier values based upon the first and a second training classifier thresholds;

determining, by one or more processors, whether the user has been exposed to the target stimuli or to the cancellation stimuli based upon the classifying of the subsequently received EEG signals into one of the first or the second range of classifier values;

calculating, by one or more processors, a hold-release classifier value based upon EEG signals received after determining whether the user has been subsequently exposed to the target stimuli or to the cancellation stimuli; and identifying, by one or more processors, whether the user has decided to hold an action associated with the target stimuli or to release the action by switching to the cancellation stimuli based on a comparison between the hold-release classifier value and the first and second training classifier thresholds.

2. The method of claim 1, further comprising:

executing, by one or more processors, one or more actions when it is determined that the user has decided to hold the action associated with the target stimuli; and stopping, by one or more processors, the execution of one or more actions when it is determined that the user has decided to release the action by switching to the cancellation stimuli.

3. The method of claim 1, wherein the act of identifying whether the user decides to hold the action comprises:

identifying the user's decision to hold the action associated with the target stimuli when the hold-release classifier value is greater than the first training classifier threshold.

4. The method of claim 1, wherein the act of identifying whether the user decides to release the action comprises:

identifying a user's decision to release the action associated with the target stimuli when the hold-release classifier value is less than the second training classifier threshold.

5. The method of claim 1, further comprising:

generating an additional hold-release classifier value based upon EEG signals received after the determination that the user has decided to hold the action associated with the target stimuli; and determining that the user has decided to hold the action associated with the target stimuli when:

the hold-release classifier value is greater than the additional hold-release classifier value;

the hold-release classifier value and the additional hold-release classifier value are both positive; and the hold-release classifier value and the additional hold-release classifier value are both less than the first training classifier threshold.

6. A non-transitory, tangible computer-readable medium storing machine-readable instructions for determining answers to a cognitive assessment test that, when executed by a processor, cause the processor to:

calculate a first and a second range of classifier values based upon a user's electroencephalograph (EEG) signals while the user is exposed to target and cancellation stimuli, respectively;

calculate a first and a second training classifier threshold to separate the first and the second range of classifier values from one another;

classify received EEG signals while the user is subsequently exposed to the target or the cancellation stimuli as being within the first or the second range of classifier values based upon the first and a second training classifier thresholds;

determine whether the user has been exposed to the target stimuli or to the cancellation stimuli based upon the classifying of the subsequently received EEG signals into one of the first or the second range of classifier values;

calculate a hold-release classifier value based upon EEG signals received after determining whether the user has been subsequently exposed to the target stimuli or to the cancellation stimuli; and identify whether the user has decided to hold an action associated with the target stimuli or to release the action by switching to the cancellation stimuli based on a comparison between the hold-release classifier value and the first and second training classifier thresholds.

7. The non-transitory, tangible computer-readable medium of claim 6, further including instructions that, when executed by the processor, cause the processor to:

execute one or more actions when it is determined that the user has decided to hold the action associated with the target stimuli; and stop the execution of one or more actions when it is determined that the user has decided to release the action by switching to the cancellation stimuli.

8. The non-transitory, tangible computer-readable medium of claim 6, wherein the instructions to identify whether the user decides to hold the selected action further include instructions that, when executed by the processor, cause the processor to:

identify the user's decision to hold the action associated with the target stimuli when the hold-release classifier value is greater than the first training classifier threshold.

9. The non-transitory, tangible computer-readable medium of claim 6, wherein the instructions to identify whether the user decides to release the selected action further include instructions that, when executed by the processor, cause the processor to:

identify a user's decision to release the action associated with the target stimuli when the hold-release classifier value is less than the second training classifier threshold.

10. The non-transitory, tangible computer-readable medium of claim 6, further including instructions that, when executed by the processor, cause the processor to:

generate an additional hold-release classifier value based upon EEG signals received after the determination that the user has decided to hold the action associated with the target stimuli; and determine that the user has decided to hold the action associated with the target stimuli when:

the hold-release classifier value is greater than the additional hold-release classifier value;

the hold-release classifier value and the additional hold-release classifier value are both positive; and the hold-release classifier value and the additional hold-release classifier value are both less than the first training classifier threshold.

* * * * *